(12) United States Patent
Borenstein et al.

(10) Patent No.: US 8,975,073 B2
(45) Date of Patent: Mar. 10, 2015

(54) MICROFLUIDIC DEVICE COMPRISING SILK FILMS COUPLED TO FORM A MICROCHANNEL

(75) Inventors: Jeffrey T. Borenstein, Newton, MA (US); Chris Bettinger, Boston, MA (US); David Kaplan, Concord, MA (US)

(73) Assignees: The Charles Stark Draper Laboratory, Inc., Cambridge, MA (US); Trustees of Tufts College, Medford, MA (US)

( * ) Notice: Subject to any disclaimer, the term of this patent is extended or adjusted under 35 U.S.C. 154(b) by 804 days.

(21) Appl. No.: 11/944,095

(22) Filed: Nov. 21, 2007

(65) Prior Publication Data

US 2009/0004737 A1 Jan. 1, 2009

Related U.S. Application Data

(60) Provisional application No. 60/860,629, filed on Nov. 21, 2006.

(51) Int. Cl.
| | | |
|---|---|---|
| C12N 5/00 | (2006.01) | |
| C12N 5/07 | (2010.01) | |
| C12M 1/00 | (2006.01) | |
| C12N 11/02 | (2006.01) | |
| A61F 2/00 | (2006.01) | |
| A61K 9/00 | (2006.01) | |
| C12Q 1/00 | (2006.01) | |
| C12M 1/34 | (2006.01) | |
| C12M 1/12 | (2006.01) | |
| B01L 3/00 | (2006.01) | |
| B81C 99/00 | (2010.01) | |
| C12M 3/06 | (2006.01) | |

(52) U.S. Cl.
CPC .......... *C12M 25/02* (2013.01); *B01L 3/502707* (2013.01); *B81C 99/0085* (2013.01); *C12M 23/16* (2013.01); *C12M 23/20* (2013.01); *C12M 29/10* (2013.01); *B01L 2200/12* (2013.01); *B01L 2300/163* (2013.01); *B81B 2201/058* (2013.01)
USPC ............. 435/395; 435/283.1; 435/284.1; 435/287.1; 435/325; 435/177; 435/4; 424/400; 424/423

(58) Field of Classification Search
CPC ........... C12M 1/00; C12M 3/00; C12M 1/34; C12M 23/16; C12M 25/00; C12N 11/02; C12N 5/00; C12N 5/06; C12N 5/0629; C12N 5/067; A61F 2/00; A61K 9/00; C12Q 1/00
See application file for complete search history.

(56) References Cited

U.S. PATENT DOCUMENTS

| | | | |
|---|---|---|---|
| 6,534,270 B2 | 3/2003 | Kim et al. | |
| 7,358,082 B2 * | 4/2008 | Tsuzuki et al. | 435/293.1 |
| 7,371,400 B2 | 5/2008 | Borenstein et al. | |
| 2002/0182241 A1 | 12/2002 | Borenstein et al. | |
| 2003/0201560 A1 | 10/2003 | Vollrath et al. | |
| 2005/0230767 A1 | 10/2005 | Park et al. | |
| 2006/0229735 A1 | 10/2006 | Roy et al. | |
| 2007/0015190 A1 | 1/2007 | Lai | |
| 2007/0123973 A1 | 5/2007 | Roth et al. | |
| 2007/0179599 A1 | 8/2007 | Brodbeck et al. | |
| 2007/0187862 A1 | 8/2007 | Kaplan et al. | |
| 2007/0212730 A1 | 9/2007 | Vepari et al. | |

FOREIGN PATENT DOCUMENTS

| | | |
|---|---|---|
| DE | 19748173 | 5/1999 |
| DE | 10-2004-008319 | 9/2005 |
| EP | 1498456 | 1/2005 |
| EP | 1511096 | 3/2005 |
| EP | 1609801 | 12/2005 |
| JP | 2006-186294 | 7/2006 |
| WO | WO-03/030194 | 4/2003 |
| WO | WO-2006/104069 | 10/2006 |
| WO | WO-2006/108684 | 10/2006 |
| WO | WO-2007/0016524 | 2/2007 |
| WO | WO-2007/0141131 | 12/2007 |

OTHER PUBLICATIONS

Altman et al. "Silk-Based Biomaterials," Biomaterials, vol. 24, Issue 3, Feb. 2003, pp. 401-416.
Bai et al., "Regenerated Spider Silk as a New Biomaterial for MEMS," Biomed. Microdevices, vol. 8, No. 4, Dec. 2006, pp. 317-323.
Bai et al., "Spider Silk as a New Biomaterial for MEMS," 19th IEEE International Conference on Micro Electro Mechanical Systems, MEMS 2006, Istanbul, Turkey, Jan. 22-26, 2006, pp. 226-229.
Bettinger et al., "Microfabrication of Poly (glycerol-sebacate) for contact guidance applications," Biomaterials, vol. 27, No. 12, Apr. 2006, pp. 2558-2565.
Bettinger et al., "Silk Fibroin Microfluidic Devices," Adv. Mater. vol. 19, Issue 19, Sep. 6, 2007, pp. 2847-2850.
Bettinger et al., "Three-Dimensional Microfluidic Tissue-Engineering Scaffolds Using a Flexible Biodegradable Polymer," Adv. Mater., vol. 18, Issue 2, Dec. 8, 2005, pp. 165-169.
Bhatia et al., "Effect of Cell-Cell Interactions in Preservation of Cellular Phenotype: Cocultivation of Hepatocytes and Nonparenchymal Cells," The FASEB Journal, vol. 13, 1999, pp. 1883-1900.
Blanchet et al., "Large Area, High Resolution, Dry Printing of Conducting Polymers for Organic Electronics," Applied Physics Letters, vol. 82, No. 3, Jan. 20, 2003, pp. 463-465.

(Continued)

*Primary Examiner* — David M Naff
(74) *Attorney, Agent, or Firm* — Edward A. Gordon; Foley & Lardner LLP

(57) ABSTRACT

A microfluidic device includes, in one embodiment, a first silk film coupled to a second silk film with at least one microchannel therebetween.

18 Claims, 10 Drawing Sheets

(56) References Cited

OTHER PUBLICATIONS

Beöhm et al., "Printable Electronics for Polymer RFID Applications," ISSCC 2006, Organic Devices and Circuits, 15.1, 2006 IEEE International Solid-State Circuits Conference, Feb. 6-9, 2006, pp. 1034-1041.
Borenstein et al., "Microfabrication Technology for Vascularized Tissue Engineering," Biomedical Microdevices, vol. 4, No. 3, Jul. 2002, pp. 167-175.
Cabodi et al., "A Microfluidic Biomaterial," J. Am. Chem. Soc., vol. 127, Issue 40, 2005, pp. 13788-13789.
Canatore et al., "A 13.56MHz RFID System Based on Organic Transponders," ISSCC 2006, Session 15, Organic Devices and Circuits, 15.2, 2006 IEEE International Solid State Circuits Conference, Feb. 6-9, 2006, pp. 1042-1051.
Chen, "Human Bone Marrow Stromal Cell and Ligament Fibroblast Responses on RGD-Modified Silk Fibers," J. Biomed. Mater. Res., vol. 67A, No. 2, Oct. 2, 2003, pp. 559-570.
Desai, "Micro- and Nanoscale Structures for Tissue Engineering Constructs," Medical Engineering & Physics, vol. 22, Issue 9, Nov. 2000, pp. 595-606.
Drury et al., "Low-Cost All-Polymer Integrated Circuits," Applied Physics Letters, vol. 73, No. 1, Jul. 6, 1998, pp. 108-110.
Duffy et al., "Rapid Prototyping of Microfluidic Systems in Poly(dimethylsiloxane)," Anal. Chem., 70, 1998, pp. 4874-4984.
Flemming et al., "Effects of Synthetic Micro- and Nano-Structured Surfaces of Cell Behavior," Biomaterials, vol. 20, No. 6, Mar. 1999, pp. 573-588.
Gawad et al., "Micromachined Impedance Spectroscopy Flow Cytometer for Cell Analysis and Particle Sizing," Lab on a Chip, vol. 1, No. 1, 2001, pp. 76-82.
Hochberg et al., "Neural Ensemble Control of Prosthetic Devices by a Human with Tetraplegia," Nature, vol. 442/13, Jul. 2006, pp. 164-171.
Hong, "A Nanoliter-Scale Nucleic Acid Processor With Paralell Architecture," Nature Biotechnology, vol. 22, No. 4, Apr. 2004, pp. 435-439.
Horan et al., "In Vitro Degradation of Silk Fibroin," Biomaterials, 26, 2005, pp. 3385-3393.
Jin et al., "Biomaterial Films of Bombyx Mori Silk Fibroin with Poly(ethlene oxide)," Biomacromolecules, 5, 2004, pp. 711-717.
Jin et al., "Elecrospinning Bombyx mori Silk with Poly(ethlyene oxide)," Biomacromolecules, 3, 2002, pp. 1233-1239.
Jin et al., "Human Bone Marrow Stromal Cell Responses on Electrospun Silk Fibroin Mats," Biomaterials, 25, 2004, pp. 1039-1047.
Jin, "Water-Stable Silk Films with Reduced β-Sheet Content," Adv. Funct. Mater., 15, 2005, pp. 1241-1247.
Kaihara et al., "Silicon Micromachining Tissue Engineer Branched Vascular Channels for Liver Fabrication," Tissue Engineering, vol. 6, No. 2, 2000, pp. 105-117.
Karageorgiou et al., "Bone Morphogenic Protein-2 Decorated Silk Fibroin Films Induce Osteogenic Differentiation of Human Bone Marrow Stromal Cells," J. Biomed. Materials, 71A, Oct. 11, 2004, pp. 528-537.
Khademhosseini et al., "Layer-by-Layer Deposition of Hyaluronic Acid and Poly-L-lysine for Patterned Cell Co-Cultures," Biomaterials, 25, 2004, pp. 3583-3592.
Kim et al., "Three-Dimensional Aqueous-Derived Biomaterial Scaffold from Silk Fibroin," Biomaterials, 26, 2005, 2775-2785.
King et al., "Biodegradable Microfluidics," Adv. Mater., 16, No. 22, Nov. 18, 2004, pp. 2007-2012.
Lecleric et al., "Study of Osteoblastic Cells in a Microfluidic Environment," Biomaterials, 27, 2006, 586-595.
Lin et al., "Pentacene-Based Organic Thin-Film Transistors," IEEE Transactions on Electron Devices, vol. 44, No. 8, Aug. 1997, pp. 1325-1331.

McGuinness et al., "Amorphous Semiconductor Switching in Melanins," Science, 183, 4127, Mar. 1, 1974, pp. 853-855.
Minoura et al., "Fine Structure and Oxygen Permeability of Silk Fibroin Membrane Treated with Methanol," Polymer, vol. 31, Feb. 1990, pp. 265-269.
Minoura et al., "Physico-Chemical Properties of Silk Fibroin Membrane as a Biomaterial," Biomaterials, vol. 11, Aug. 1990, pp. 430-434.
Nijst et al., "Syntheses and Characterization of Photocurable Elastomers from Poly (glycerol-co-sebacate)," Biomacromolecules, 8, 2007, pp. 3067-3073.
Paguirigan et al., "Gelatin Based Microfluidic Devices for Cell Culture," Lab Chip, 6, 2006, pp. 407-413.
Perez-Rigueiro et al., "Mechanical Properties of Single-Brin Silkworm Silk," Journal of Polymer Science, vol. 75, Issue 10, Feb. 7, 2000, pp. 1270-1277.
Pins et al., "Microfabrication of an Analog of the Basal Lamina: Biocompatible Membranes with Complex Topographies," The FASEB Journal, vol. 14, No. 3, Mar. 2000, pp. 593-602.
Richards Grayson et al., "Multi-Pulse Drug Delivery from a Resorbable Polymeric Microchip Device," Nature Materials, vol. 2, Issue 11, Nov. 2003, pp. 767-772.
Richardson et al. "Polymeric System for Dual Growth Factor Delivery," Nature Biotechnology vol. 19, Nov. 2001, pp. 1029-1034.
Rivers et al., "Synthesis of a Novel Biodegradable Electrically Conducting Polymer for Biomedical Applications," Adv. Funct. Mater., vol. 12, Issue 1, Jan. 2002, pp. 33-37.
Rujiravanit et al., "Preparation of Crosslinked Chitosan/Silk Fibroin Blend Films for Drug Delivery System," Macromol. Biosci. 3, Issue 10, 2003, pp. 604-611.
Santini, Jr. et al., "A Controlled-Release Microchip" Nature, vol. 397, Issue 6717, Jan. 28, 1999, pp. 335-338.
Sofia et al., "Functionalized Silk-Based Biomaterials for Bone Formation," Journal of Biomedical Materials Research, vol. 54, Issue 1, Nov. 1, 2000, pp. 139-148.
Suh et al., "A simple soft lithographic route to fabrication of poly-(ethylene glycol) microstructures for protein and cell patterning," Biomaterials, vol. 25, No. 3, Sep. 10, 2003, pp. 557-563.
Tsukada et al., "Structural Changes of Silk Fibroin Membranes Induced by Immersion in Methanol Aqueous Solutions," Journal of Polymer Science: Part B: Polymer Physics, vol. 32, No. 5, 1994, pp. 961-968.
Vepari et al., "Covalently Immobilized Enzyme Gradients Within Three-Dimensional Porous Scaffolds," Biotechnol. Bioeng., vol. 93, No. 6, 2006, pp. 1130-1137.
Wang et al., "A Tough Biodegradable Elastomer," Nature Biotechnology, vol. 20, Issue 6, Jun. 2002, pp. 602-606.
Weinberg et al., "Design and Fabrication of a Constant Shear Microfluidic Network for Tissue Engineering," Materials Research Society, Symposium Proceedings, vol. 280, Nanoengineered Assemblies and Advanced Micro/Nanosystems, Apr. 13-16, 2004, pp. 121-126.
Zelikin et al., "Erodible Conducting Polymers for Potential Biomedical Applications" Angew. Chem. Int. Ed., vol. 41, No. 1, 2002, pp. 141-144.
International Search Report for PCT Application No. PCT/US2007/024314, mailed Sep. 3, 2008, 6 pages.
Written Opinion for PCT Application No. PCT/US2007/024314, mailed Sep. 3, 2008, 8 pages.
Li, et al. "Study on Porous Silk Fibroin Materials. II. Preparation and Characteristics of Spongy Porous Silk Fibroin Materials", Journals of Applied Polymer Science, Mar. 21, 2001, vol. 79, No. 12, pp. 2192-2199.
Min, S. et al. "Preparation and Characterization of Crosslinked Porous Silk Fibroin Gel", Sen 'l Gakkaishijournal of the Society of Fiber and Tech, 1998, vol. 54, No. 2, pp. 85-92.
Nazarov, et al. "Porous 3-D Scaffolds from Regenerated Silk Fibroin", Biomacromolecules, May/Jun. 2004, vol. 5, No. 3, pp. 718-726.

* cited by examiner

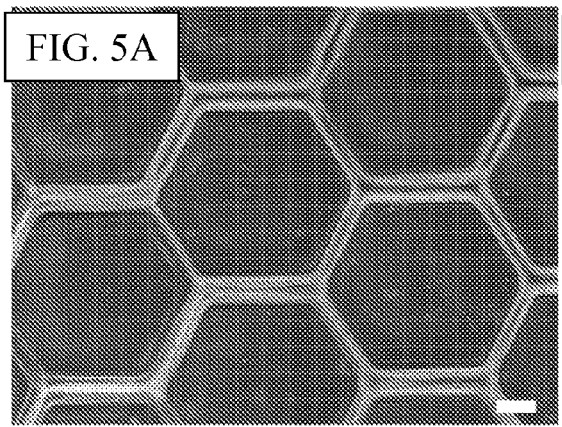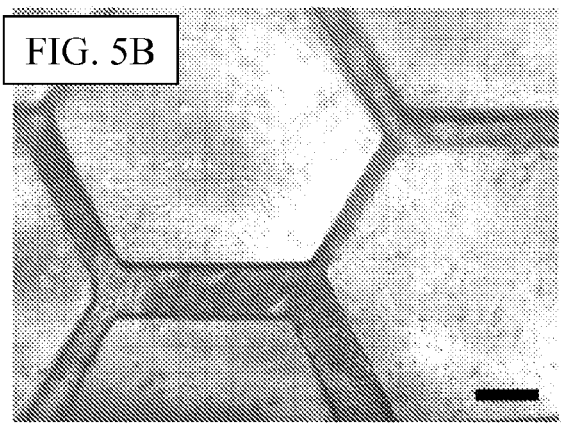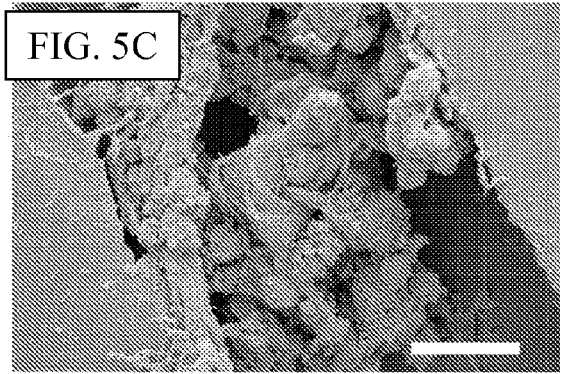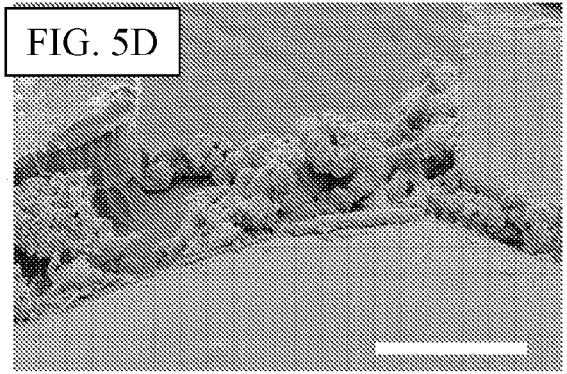

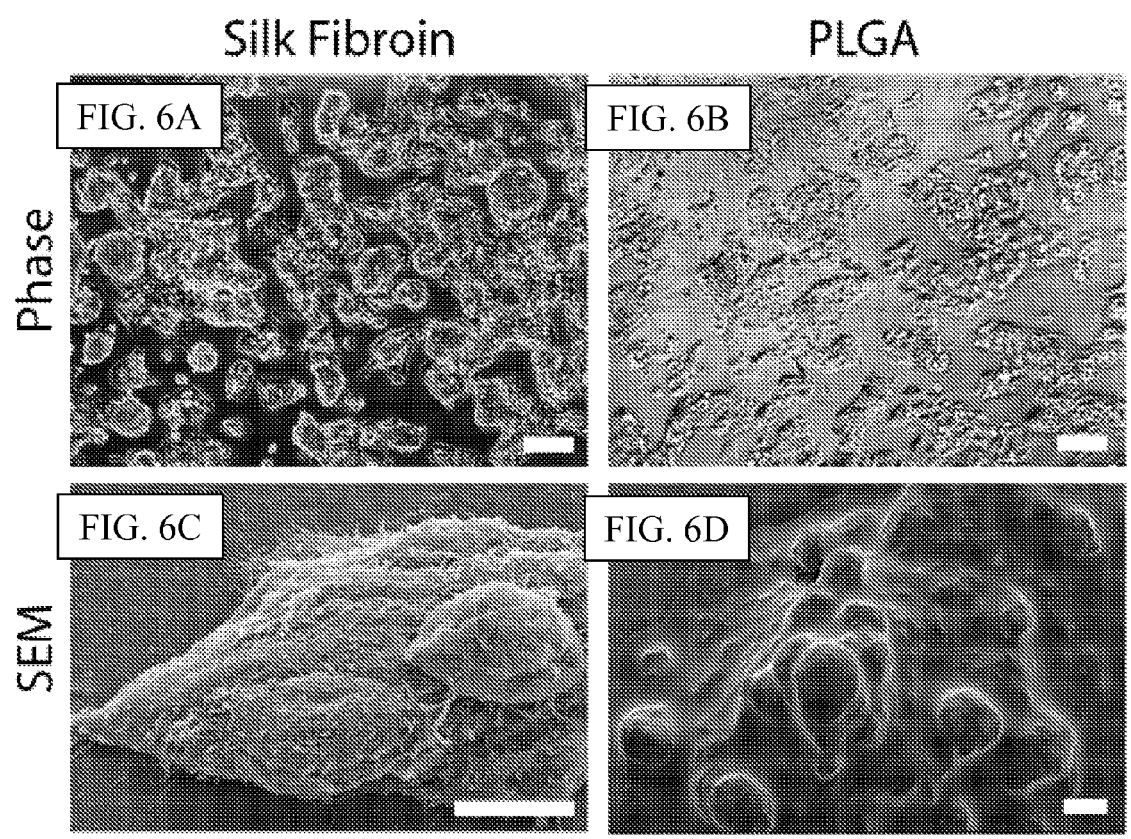

| Ra (nm) | Rq (nm) | Rz (um) | Rt (um) |
|---------|---------|---------|---------|
| 216.6 | 267.4 | 1.4321 | 1.5822 |

MICROFLUIDIC DEVICE COMPRISING SILK FILMS COUPLED TO FORM A MICROCHANNEL

CROSS-REFERENCE TO RELATED APPLICATIONS

The present application claims the benefit of and priority to U.S. Provisional Patent Application No. 60/860,629, filed Nov. 21, 2006, the disclosure of which is incorporated herein by reference in its entirety.

STATEMENT REGARDING FEDERALLY SPONSORED RESEARCH OR DEVELOPMENT

The U.S. Government may have certain rights in this invention as provided for by the terms of U.S. Army Contract No. DAMD17-02-2-0006, awarded by the Center for Integration of Medicine and Innovative Technology, and Grant No. NIH R01-DE-013023-06, awarded by the National Institute of Health.

TECHNICAL FIELD

The invention generally relates to silk-based systems and devices, such as biodegradable micro-electro-mechanical biomedical devices, and methods for fabricating the same. More particularly, the invention relates to microdevices, such as microfluidic devices, comprising silk materials, such as silk fibroin, and to methods for fabricating the same.

BACKGROUND

Biomedical research has increasingly moved towards the design and implementation of microfabricated systems to efficiently improve technologies such as drug delivery, diagnostics, and tissue engineering. It is known that biological interactions vary significantly at different length-scales. Technologies featuring micron length-scales tailored specifically for biomedical applications, termed biomicroeiectromechanical systems ("BioMEMS"), are able to interact with biological systems such as cells or even single biomolecules. Previous strategies for developing BioMEMS have typically focused on using traditional non-degradable materials. For example, the strategies have typically involved adapting traditional microfabrication materials and processes, thereby resulting in systems fabricated from non-degradable materials such as silicon and polydimethylsiloxane ("PDMS"). However, non-degradable materials are often not suitable for implantable/biomedical applications and may present health and safety concerns.

There have also been previous studies using biomaterials, such as biodegradable polymers, as there is a growing demand for implantable BioMEMS in in vivo applications, such as drug-delivery systems and tissue engineering. For example, BioMEMS devices have been fabricated using biopolymers, both natural and synthetic, including gelatin, alginate, poly(L-lactic acid) ("PLA"), poly(L-lactic-co-glycolic) acid ("PLGA"), and poly(glycerol-co-sebacate) ("PGS"). However, the above-mentioned biodegradable materials are often found to have poor mechanical, electrical, and biological properties, undesirable biodegradation kinetics, and limited chemical functionality for implantable biomedical device applications.

SUMMARY OF THE INVENTION

In various embodiments, the present invention relates to the microfabrication of silk structures in systems and devices. The unique mechanical properties of reprocessed silk, such as fibroin, its biocompatibility, and its biodegradability make silk fibers attractive for use in biotechnological materials and medical applications. Embodiments of the present invention differ from the prior art in that they utilize silk materials, such as silk fibroin and modified silk fibroin, a fully biodegradable protein-based biomaterial, to fabricate a biodegradable microfluidic device. For example, microfluidic devices may be fabricated from silk using an aqueous molding process adapted from soft lithography. In some embodiments, the resulting devices are mechanically robust and possess microchannels for passing fluid through the device. Hepatocytes may also be seeded in the device to deliver liver-specific functions equivalent to those observed for standard tissue culture substrates. Other microstructures may also be fabricated in the silk films and layers of the device. For example, embodiments of the present invention allow for the fabrication of silk-based films and layers into nanometer-scale posts defining microchannels therebetween, micrometer-scale microwalls defining microchannels therebetween, and micrometer-scale raised platforms separated by depressions or microchannels therebetween.

Embodiments of the present invention feature several advantages over former approaches, including the fact that devices may be constructed using silk, for example fibroin, and therefore be fully biodegradable. In contrast, many existing devices are not fully degradable and therefore may have adverse health, environmental, safety, and security considerations, depending upon the application. In addition, silk offers a wide range of advantages in terms of a microfabricated material for BioMEMS applications. Silk, such as silk fibroin from the Bombyx mori silkworm, is FDA-approved, exhibits in vitro and in vivo biocompatibility, as well as robust mechanical properties including a high mechanical modulus and toughness, and relatively slow, protease-mediated, proteolytic biodegradation. Accordingly, embodiments of the present invention, fabricated with the advantageous physical properties of resorbable silk, may involve various systems and devices, for example BioMEMS systems, useful for in vivo sensor and drug-delivery applications.

Accordingly, in one aspect, the invention relates to a microfluidic device having first and second silk films coupled to define at least one microchannel therebetween. One or both of the silk films may include silkworm silk (such as silk fibroin), spider silk, and/or genetically engineered variants of silks. In certain embodiments, the microchannel is molded into the first silk film. Alternatively, the microchannel may be formed from features molded into both the first and second silk films, so that the microchannel is completed when the two films are coupled together. At least a portion of the first silk film may be bonded to a portion of the second silk film, for example, by laminating a portion of the two films together with a silk solution, optionally in combination with heat and/or pressure. In certain embodiments, an interface between the first and second silk films is water-insoluble. The microchannel may be enclosed about its axis, optionally with open inlet and outlet.

The devices may be fabricated to support the growth of cells, for example eukaryotic cells, such as hepatocyte. In certain embodiments, a portion of a surface of the microchannel supports cell growth, optionally in their native morphology.

More than one microchannel may be present in a microfluidic device. Accordingly, in certain embodiments, the first and second silk fibroin films define a plurality of microchannels therebetween. Each microchannel may be, for example, less than 500 micrometers in diameter. At least some of the microchannels may be in fluidic communication. In addition, at least a portion of the plurality of microchannels may appear as a repeated a geometric pattern. The repeated geometric pattern may provide for a constant maximum shear stress at a steady volumetric flow rate within all the microchannels.

In another aspect, the invention relates to a microdevice for use in growing cells and includes a silk layer having a plurality of molded microfeatures formed therein or thereon. Each of the molded microfeatures may be less than 500 micrometers in diameter, and the plurality of molded microfeatures may delineate regions on the silk layer that support cell growth. In various embodiments, the microfeatures are microchannels, posts, microwalls, and/or raised platforms. The microdevice may be biodegradable.

In still another aspect, the invention relates to a method for fabricating a microfluidic device including applying a silk solution to a negative mold, evaporating solvent from the solution to form a micromolded silk film, removing (e.g., delaminating) the micromolded silk film from the negative mold, and laminating the micromolded silk film to at least one additional layer to form a microfluidic device having at least one enclosed microchannel. The additional layer(s) may include silk. The silk solution, silk film, and/or additional layer(s) may include silkworm silk (such as silk fibroin), spider silk, and/or genetically engineered variants of silks. Moreover, the silk solution may be an aqueous solution, and organic solvent, or a combination thereof. The negative mold may impart a plurality of microchannels into the micromolded silk fibroin film. Each molded microchannel may be, for example, less than 500 micrometers in diameter.

In another aspect, the invention relates to a method for transporting fluid including providing a microfluidic device having a microchannel formed in a silk film. The microchannel has an inlet and an outlet and the fluid is transported along the microchannel from the inlet to the outlet. The silk film may include silkworm silk (such as silk fibroin), spider silk, and/or genetically engineered variants of silks. The microchannel may be, for example, less than 500 micrometers in diameter.

In yet another aspect, the invention relates to a method for growing cells including providing a microfluidic device having a microchannel formed in a silk film, flowing cell culture medium through the microchannel, and seeding cells into the microchannel to allow the cells to adhere to a surface of the microchannel. The silk film may include silkworm silk (such as silk fibroin), spider silk, and/or genetically engineered variants of silks.

BRIEF DESCRIPTION OF THE DRAWINGS

The foregoing and other objects, aspects, features, and advantages of the invention will become more apparent and may be better understood by referring to the following description taken in conjunction with the accompanying drawings.

FIGS. 5A-5D are micrographs of various illustrative embodiments of cell-seeded silk-fibroin microfluidic devices in accordance with the invention.

FIGS. 6A-6D are phase and scanning electron micrographs comparing morphology of HepG2 cells cultured on silk fibroin to those cultured on PLGA.

DETAILED DESCRIPTION

Figure 1A:
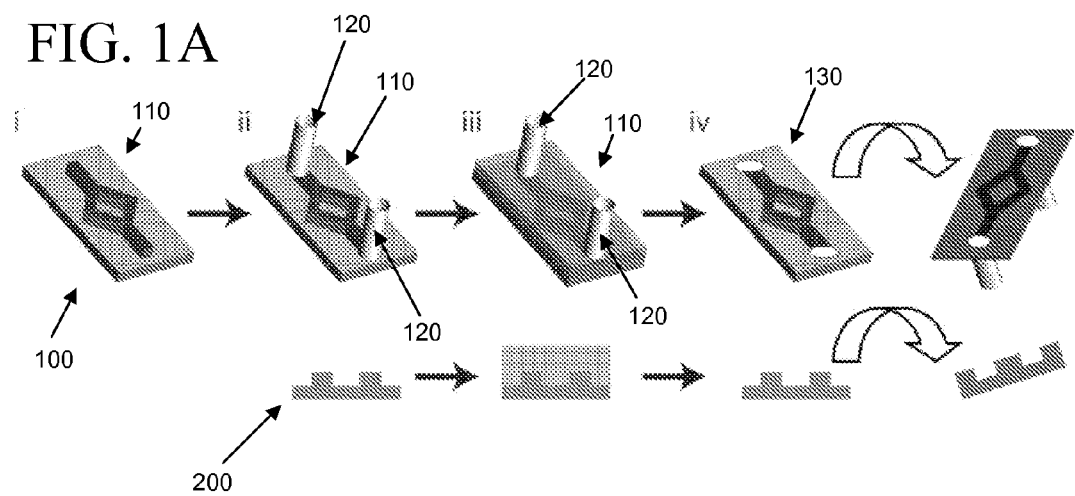
FIGS. 1A and 1B are flow diagrams of an illustrative embodiment of a method for fabricating a silk fibroin based microfluidic device in accordance with the invention.

In general, embodiments of the present invention pertain to silk-based systems and devices, such as biodegradable MEMS biomedical devices, and methods for fabricating the same. For example, embodiments of the invention relate to microdevices, such as microfluidic devices, comprising silk materials, such as silk fibroin, and to methods relating thereto.

From a material properties standpoint, an ideal biomaterial for BioMEMS fabrication is one that: 1) may be processed using mild conditions to facilitate protein or growth factor incorporation; 2) naturally promotes adhesion and normal function of seeded cells; 3) contains moieties for potential chemical modification of the surface; 4) exhibits slow and predictable degradation rates to maximize duration of functional implanted devices; 5) has robust, yet flexible mechanical properties; and 6) is relatively inexpensive. One class of natural biomaterial that addresses these requirements for implantable BioMEMS device fabrication is silk material. For example, silk fibroin protein from the Bombyx mori silkworm is FDA-approved and exhibits in vitro and in vivo biocompatibility, robust mechanical properties including high mechanical modulus and toughness, and relatively slow, protease-mediated, proteolytic biodegradation.

Described below are techniques and materials-processing strategies utilized in the fabrication of silk microdevices, such as microfluidic devices that have microfeatures (e.g., microchannels, posts, a microwalls, or raised platforms). For example, a microfluidic device may be fabricated from first and second silk films that are coupled together to define at least one microchannel therebetween. As another example, a multilayer device that includes a silk layer and a second layer may be fabricated and used to grow cells. The silk layer may include a pattern of microchannels formed therein and a portion of the second layer may be coupled to a portion of the silk layer.

The fabrication techniques and strategies include material-specific processes for silk micromolding and device assembly that are analogous to soft-lithographic techniques. By implementing aqueous casting of regenerated aqueous silk solutions to produce microfabricated silk films and/or layers, the use of toxic solvents and harsh processing conditions may be avoided. In certain embodiments, microdevices are fabricated by laminating water-stable micromolded silk films having high precision microfeatures, such as microchannels, posts, microwalls, and/or raised platforms separated by fluidic channels. In another embodiment, microfluidic devices with seeded cells are perfused with a model human hepatocarcinoma cell line for up to five days. Such hepatocytes cultured in silk based microfluidic devices may exhibit similar morphology and cell functions to those grown on other widely used biomaterials.

1. Silk

Silk is a well-characterized natural fiber produced from various sources, for example, silkworms, spiders, and genetic engineering. Silk has been used for threads in textiles for thousands of years. Many silks contain a fibrous protein termed "fibroin" (both heavy and light chains) that form the thread core, and glue-like proteins termed "servicing" that surround the fibroin fibers to cement them together. The fibroin is a highly insoluble protein containing up to 90% of the amino acids glycine, alanine and serine, leading to beta-pleated sheet formation in the fibers.

Silk fibroin includes silkworm fibroin. Silk may be obtained from various natural sources, for example from the silkworm Bombyx mori or from the spider Nephila clavipes. Silk solutions used in accordance with embodiments of the present invention may be obtained, for example, from a solution containing a dissolved silkworm silk (e.g. from Bombyx mori), a dissolved spider silk (e.g. from Nephila clavipes), or from a solution containing a genetically engineered silk, such as from bacteria, yeast, mammalian cells, transgenic animals, or transgenic plants.

2. Microfabrication of a Silk-Based Microfluidic Device

In various embodiments, the microfluidic devices described herein include silk films and/or silk layers comprising one or more microchannels. The silk films and/or silk layers may be fabricated by applying a silk solution to a mold or a negative mold comprising a feature that is transferred as a microchannel to the silk film or layer. The molded silk film or layer also may be coupled to a second layer, for example, to further define and/or enclose the microchannel.

2.1. Mold

Molds may be produced by any suitable technique known in the art. For example, molds may be formed by micromachining silicon, glass, ceramics, or other wafer materials, or by using electroforming, photolithography (e.g., thick photoresist processing), or other mold production techniques, for example, forms of lithography such as nanoimprint lithography, interference lithography, X-ray lithography, extreme ultraviolet lithography, and scanning probe lithography. Subsequent molds may be produced by repeating the micromachining process. In certain embodiments, silk films and/or silk layers comprising one or more microchannels may be fabricated directly from such a mold by applying a silk solution to the mold and allowing the solution to solidify. It is understood that, in such a fabrication technique, a feature of the mold will impart a negative of the feature to a silk film and/or layer. For example, a wall appearing on the mold will appear as a channel in the silk film and/or layer. Accordingly, silk films and layers may be generated with any feature that can be imparted from a mold, for example posts, microwalls, raised platforms, and/or microchannels.

Figure 2A:
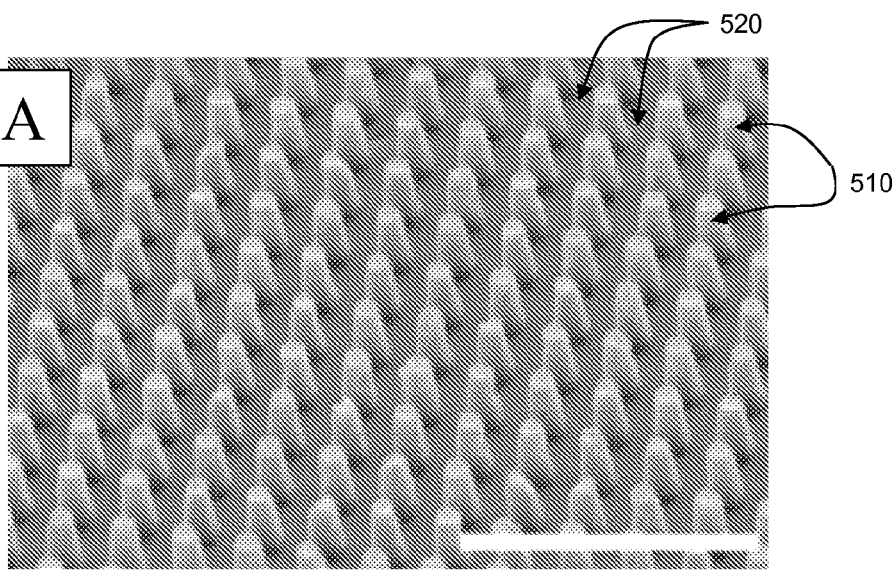
FIGS. 2A-2C are micrographs illustrating various exemplary features of silk fibroin-based microfluidic devices in accordance with the present invention.
Figure 2B:
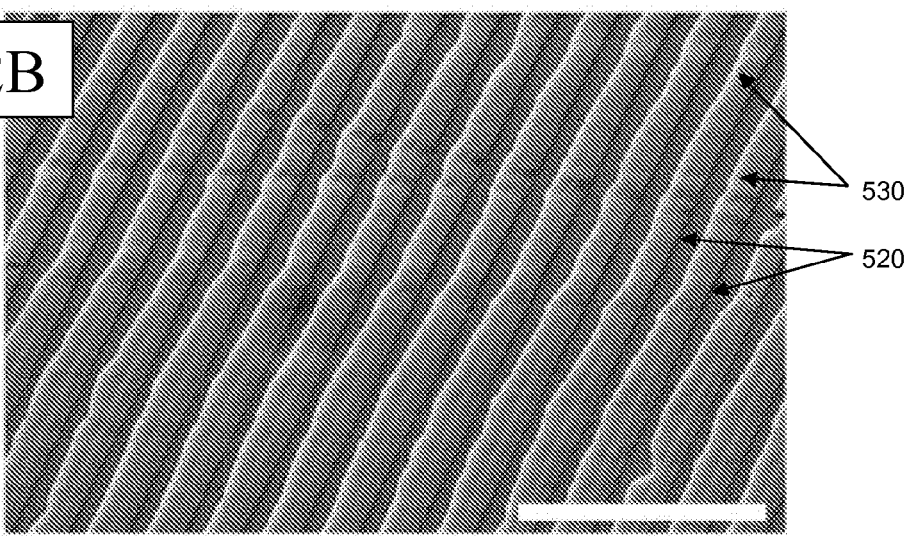
Figure 2C:
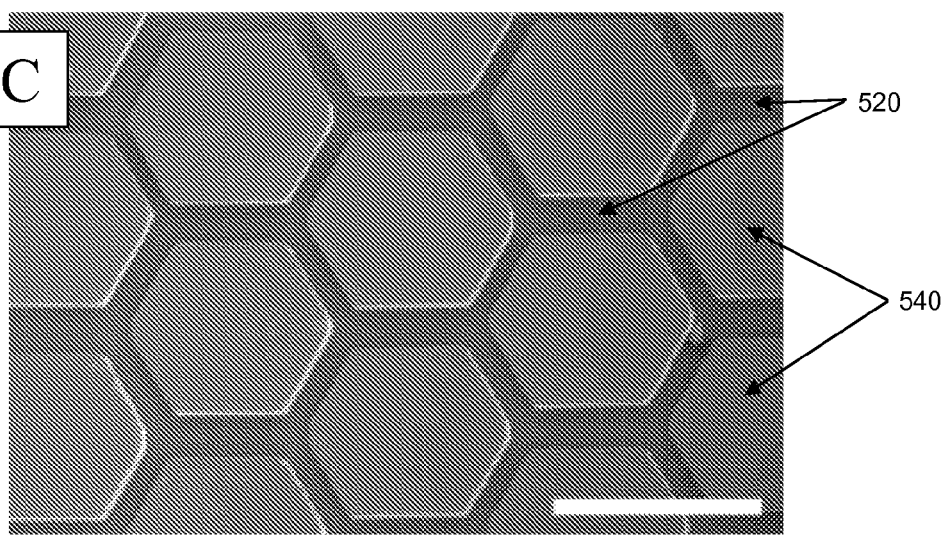

In certain embodiments, soft lithography techniques may be used to generate a polymeric negative mold from a positive mold prepared, for example, as described in the previous paragraph. For example, once a positive mold is formed, suitable polymer material may be delivered onto the positive mold. A polymeric negative mold is allowed to solidify and is delaminated from the positive mold. The form of the positive mold may be prepared with any number of patterns, which will impart the negative pattern to the negative mold. The negative mold then will impart the same or a similar feature as on the positive mold to the silk film or silk layer that is fabricated from the negative mold. For example, a positive mold may be produced with features such as nanometer-scale posts defining microchannels therebetween, micrometer-scale microwalls defining microchannels therebetween, and/or raised platforms separated by a network of depressions or microchannels therebetween. The negative of these features then will transfer to a negative mold and the same or similar features as on the positive mold will transfer from the negative mold to the a silk film or layer. Such features are shown in FIGS. 2A-2C. Accordingly, it is understood that any feature that can be applied to a positive mold and transferred to a negative mold (as a negative feature) may be produced in a silk film or layer fabricated from the negative mold. Subsequent negative molds may be produced by repeating the soft lithography technique with the same or a new positive mold.

Any polymer known in the art may be used to generate a negative mold. By way of example, a PDMS negative mold may be generated using Du Pont SYLGARD and a SU-8 high-aspect-ratio negative photoresist. The materials and devices that may be used to generate such a negative mold are SU-8 negative epoxy-based photoresist (supplied by Microchem Co.), a micromachined silicon wafer, a spinner, a hotplate, a UV exposure tool, a photomask, and a propylene glycol monomethyl ether acetate (PGMEA) organic solvent developer (also called XPS). To create a spin resist, two-thirds of the wafer radius may be covered with the SU-8 resist, and the resist may be allowed to flow for 3-5 seconds. Then, the spinner speed may be ramped from 100 rpm/second to 500 rpm/second, and then instantaneously ramped to a desired spin speed. The initial ramp allows spreading and wetting of the substrate surface. As a guide, the number after SU-8 (i.e. SU-850) indicates the resulting film thickness when spun at 2500 rpm. To softbake, the micromachined wafer may be placed on a hotplate at room temperature with a slow ramp to 95° C., which is above the glass transition temperature. The hotplate should be planarized, because the resist will flow and correct some of the film imperfections (i.e., bubbles and topology). Because the resist is soft at 95° C., the film may pick up particles from the air, so it is preferred to make a small covering for each wafer out of tin foil. The temperature may be ramped down after 3 hours and then the resist may be exposed to the micromachined wafer for 5-20 minutes.

The next step is a post exposure bake. Starting at room temperature, the temperature may be ramped to 95° C. with the wafer on hot plate, as was done in the softbake step, described above. This may be baked for 1 hour. Finally, the polymeric material may be developed in PGMEA organic solvent, with gentle and frequent mixing, with a final rinse in isopropyl alcohol. A white scum may appear, because dissolved SU-8 tends to stay at the surface of the wafer. Then, the mold may be returned to the bath for a minute, with this step repeated several times until the white scum is gone. Organic residues may remain, so to clean fully, the wafer may be rinsed quickly in acetone, then quenched in isopropyl alcohol. The organic monomers may be removed with a quick distilled water rinse and quenched once more with isopropyl alcohol. The mold may be dried with nitrogen gas and the PDMS negative mold may be delaminated from the positive mold. Further details on the fabrication of the negative molds are set forth in, for example, United States Patent Application Publication Nos. 2002/0182241 and 2003/0003575, the disclosures of which are incorporated herein by reference in their entirety.

2.2. Preparation of Silk Solution

The silk fibroin solution that is applied to the mold or negative mold may be prepared by any conventional method known to one skilled in the art. For example, Bombyx mori cocoons may be boiled for about 30 minutes in an aqueous solution, such as an aqueous solution having about 0.02M Na$_2$CO$_3$. The cocoons may be rinsed, for example with water, to extract the sericin proteins, and the extracted silk may be dissolved in an aqueous salt solution. Salts useful for this purpose include lithium bromide, lithium thiocyanate, calcium nitrate, or other chemicals capable of solubilizing silk. The extracted silk may be dissolved in about 9-12 M LiBr solution and the salt consequently removed using, for example, dialysis.

If necessary, the solution may then be concentrated using, for example, dialysis against a hygroscopic polymer, for example PEG, a polyethylene oxide, amylose or sericin. This tends to generate thicker films. The PEG may be of a molecular weight of 8,000-10,000 g/mol and may have a concentration of 25-50%. A slide-a-lyzer dialysis cassette (Pierce, MW CO 3500) may be used for the dialysis; however, any dialysis system may be used. The dialysis may be performed for a time period sufficient to result in a final concentration of aqueous silk solution between about 15-30%, 10-20%, 5-15%, 5-10%, less than 10%, about 8%, or from about 5% to about 8%. Further details on the preparation of aqueous silk solutions are set forth in, for example, United States Patent Application Publication No. 2007/0187862 and PCT Application Publication No. WO 2007/016524, the disclosures of which are incorporated herein by reference in their entirety.

Alternatively, the silk solution may be produced using organic solvents. Such methods have been described in, for example, Li, M., et al., J. Appl. Poly Sd. 2001, 79, 2192-2199; Min, S., et al. Sen 'I Gakkaishi 1997, 54, 85-92; and Nazarov, R. et al., Biomacromolecules 2004 May-June; 5(3):718-26, the disclosures of which are incorporated herein by reference in their entireties. However, the use of organic solvents in the preparation of silk materials can alter the biocompatibility of silk materials exposed to cells in vitro or in vivo. Organic solvents may also change physical properties of silk material. For example, the immersion of silk films in organic solvents such as methanol may cause dehydration of the hydrated or swollen structure, leading to crystallization and thus, loss of solubility in water. Further, the use of organic solvents can render the silk material to be less degradable.

In accordance with this methodology, micromolded silk fibroin films cast on PDMS negative molds may be produced in rapid succession while maintaining a high degree of feature fidelity. For example, features as small as 100 nanometers may be produced using this method.

2.3. Silk Film and/or Layer Fabrication

Figure 1B:
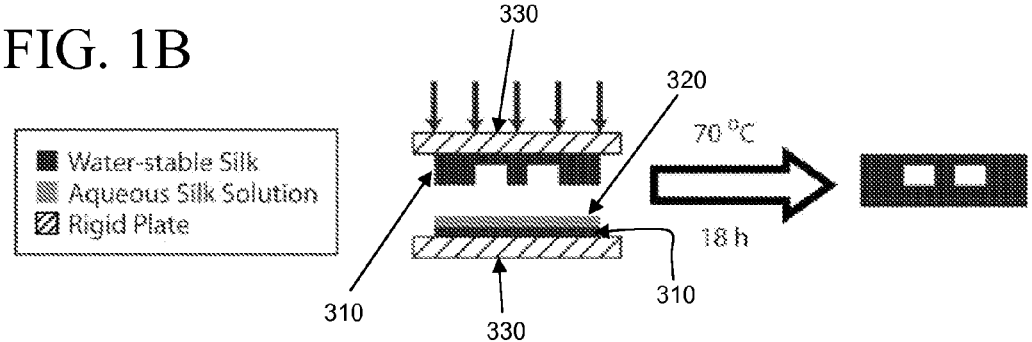

After the mold has been formed and the silk solution has been prepared, the silk solution is applied to the mold (e.g., a negative mold). The silk solution is allowed to solidify and then is delaminated from the mold. The resulting silk film and/or layer will have a preselected pattern of microfeatures, for example, microchannels, depending on the features of the mold. FIGS. 1A and 1B depict flow diagrams of a method for fabricating silk fibroin microfluidic devices comprising microchannels, according to an illustrative embodiment of the invention.

In FIG. 1A, the process flow is diagrammed in both an isometric view 100 and a cross-sectional view 200 through the midline for the successive steps of the process. PDMS negative molds 110 may be fabricated (step i) using traditional soft lithography techniques, for example as described above. The PDMS molds 110 optionally may be modified with tubing, for example, silicon tubing 120 (step ii) or silk tubing, prior to solvent casting of the silk solution (step iii). Upon evaporation of the solvent (e.g., water), ionic liquids, organic solvents, or other liquids that enable the processing and construction of silk-based microfluidic devices, micromolded films 130 may be delaminated with integrated fluidic connections (step iv). Both micromolded and flat silk films may then be treated with aqueous methanol solutions.

Figure 3A:
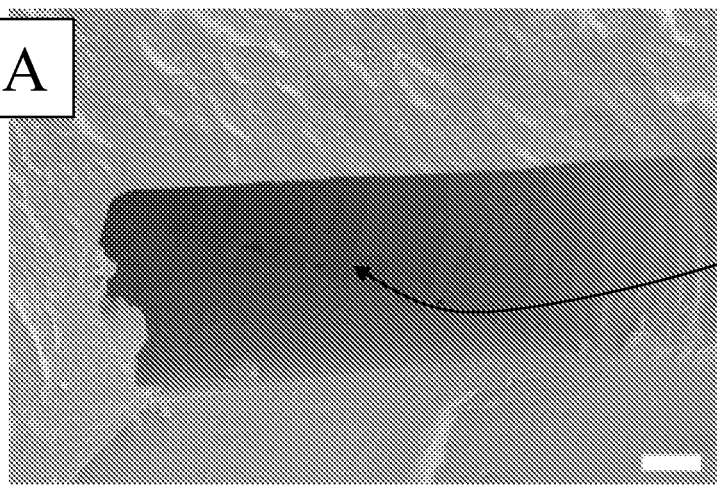
FIGS. 3A-3C are micrographs illustrating microchannels in an exemplary microfluidic device.
Figure 3B:
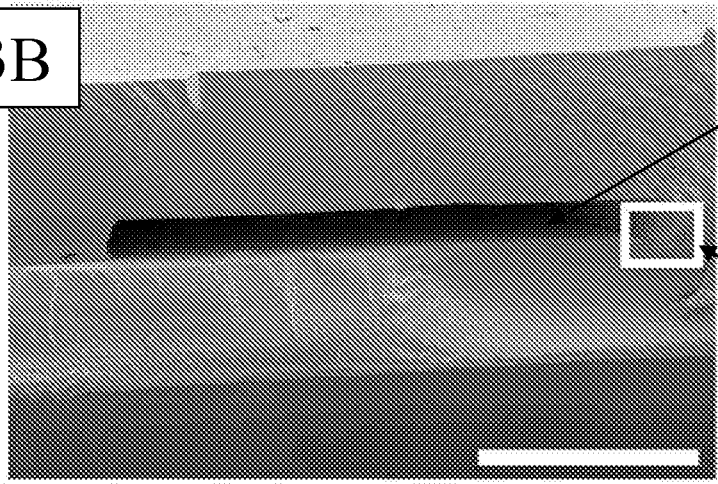
Figure 3C:
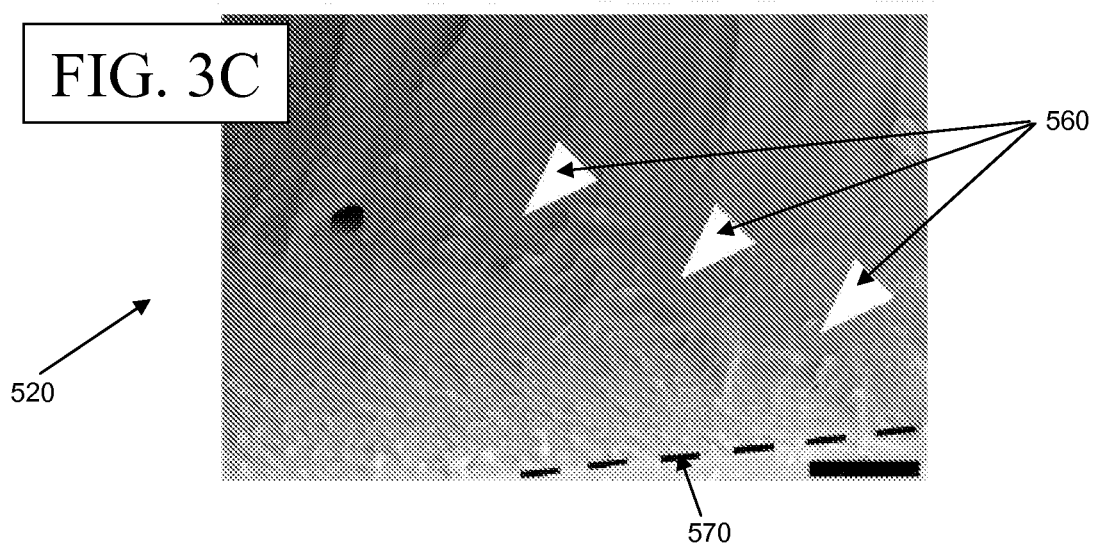
Figure 3D:
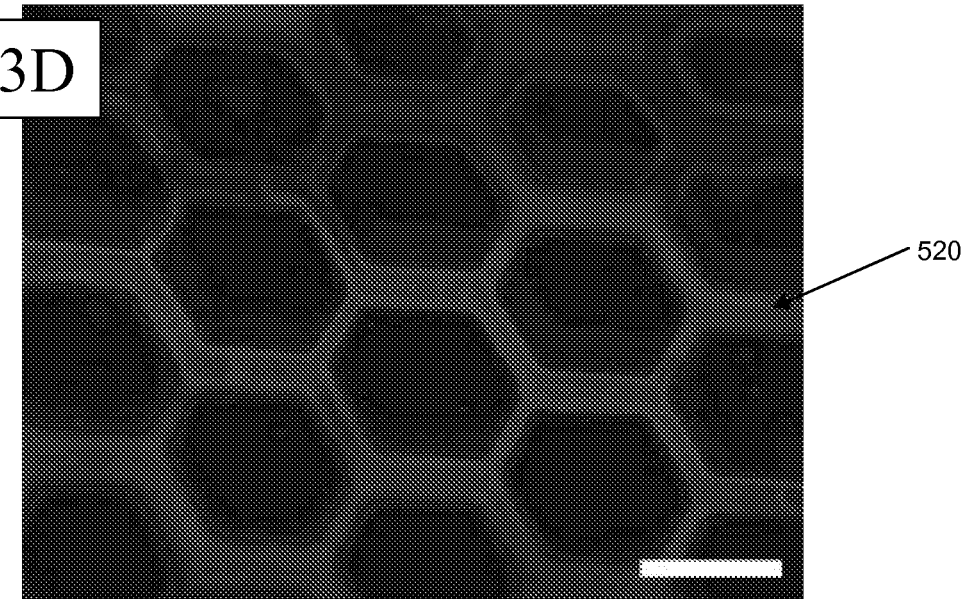
FIGS. 3D and 3E are fluorescent micrographs of patent microfluidic devices perfused with rhodamine solution to indicate retention of the perfusate within the microchannels.
Figure 3E:
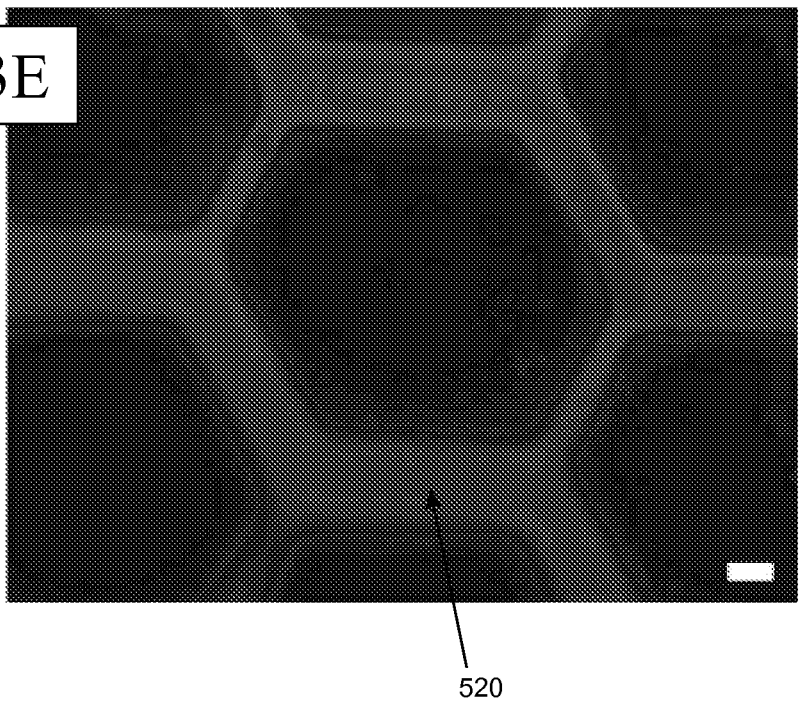

The silk fibroin micromolded films 130 may be bonded together. Bonding may be achieved by any suitable method known in the art, for example, lamination by adhesive, heat, mechanical pressure, and/or chemical alteration. For example, as depicted in FIG. 1B, appropriate water-stable silk films and/or layers 310 may be bonded using additional regenerated aqueous silk solution 320. In one embodiment, silk layers are bound between rigid plates 330 under mechanical pressure at 70° C. for 18 hours to produce a water-insoluble silk interface with increased β-sheet content. Photomicrographs of bonded silk films are shown in FIGS. 3A-3C. Photomicrographs of fluid perfused through the microchannels enclosed by the bonding are shown in FIGS. 3D-3E. In some embodiments, the second film or layer may include the same composition of silk as the first layer, a different composition of silk as the first layer, or no silk at all.

3. Microfluidic Device Properties and Features

Embodiments of the methods of the present invention allow for fabrication of silk films and layers with various properties and features.

3.1. Controlling the Properties of the Silk-Based Microdevice

As noted above, dialyzing the silk solution against a hygroscopic polymer tends to generate a thicker film or layer. Moreover, the presence of organic solvents, as compared to aqueous solvents, in the silk solution, may generate silk films and/or layers with more crystalline structure, as compared to amorphous structure. This phenomenon may be used to control, for example, the rate of biodegradation of the silk-based microdevice and/or mechanical properties. Accordingly, depending on the desired features for the silk film and/or layer, the silk solution may be prepared using any suitable ratio of aqueous/methanol solution, for example, 100% aqueous, about 80% aqueous, about 60% aqueous, about 50% aqueous, about 40% aqueous, about 20% aqueous, or about 10% aqueous.

Figure 4A:
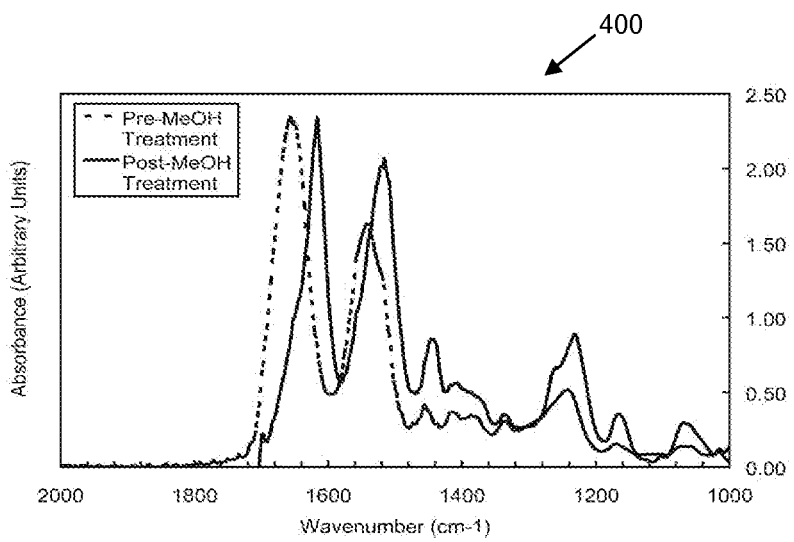
FIGS. 4A-4C are graphs illustrating various physical properties of methanol-treated silk-fibroin films in accordance with the invention.
Figure 4B:
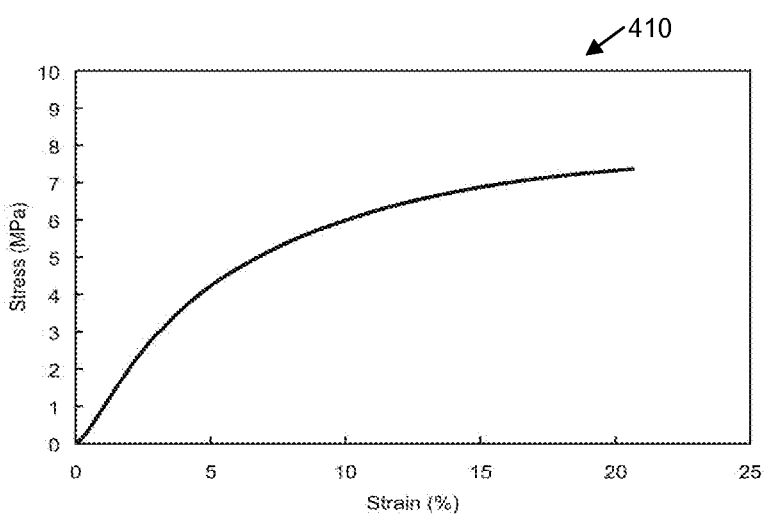
Figure 4C:
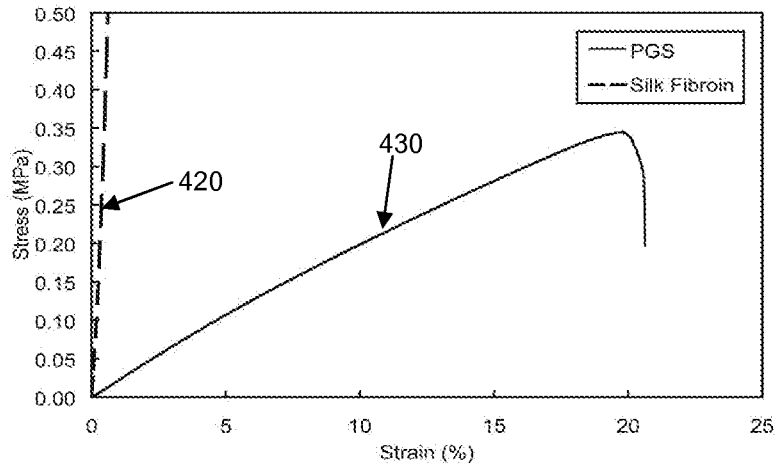

In one embodiment, with reference to the graph 400 depicted in FIG. 4A, FT-IR on silk films cast from regenerated aqueous silk fibroin solution exhibited peaks for amide II (at 1656.6 cm$^{-1}$) and amide II of random or silk I structure (at 1541.5 cm$^{-1}$), in addition to other peaks at 1456.4 cm$^{-1}$, and 1243.0 cm$^{-1}$. However, silk films treated with aqueous methanol solutions exhibited a shift to a crystalline silk II structure as observed in peak shifts in amide I (1616.3 cm$^{-1}$) and amide II (1515.6 cm$^{-1}$) functionalities. Additional peaks were observed at 1445.3 cm$^{-1}$ and 1231.6 cm$^{-1}$. With reference to the representative tensile stress versus engineering strain curve 410 depicted in FIG. 4B, hydrated, water-stable silk fibroin films exhibited relatively high stiffness and toughness with a significant region of plastic deformation. FIG. 4C indicates the representative tensile stress versus engineering strain curves of one embodiment of a silk film, a silk fibroin film, (curve 420) compared to PGS films (curve 430). Table 1 below includes related numerical data.

Additional techniques known in the art, for example crosslinking, may be used to control the degradation rate and mechanical properties of the silk film and/or layer. Alternatively, the silk film and/or layer may be drawn or stretched mono-axially or biaxially. The stretching of a silk blend film may induce molecular alignment of the film and thereby improve the mechanical properties of the film.

3.2. Physical Features of the Microdevice

Embodiments of the present invention allow for fabrication of microdevices comprising highly precise and reproducible features of micron and sub-micron resolution. For example, replica molded silk films may be fabricated to have the features depicted in FIGS. 2A-2C. In particular, FIG. 2A shows nanometer-scale posts 510 with minimum widths of approximately 400 nm. The posts 510 define microchannels 520 therebetween. The scale bar in FIG. 2A is 5 microns. FIG. 2B depicts micrometer-scale microwalls 530 defining fluidic channels 520 therebetween. The scale bar in FIG. 2B is 5 microns. FIG. 2C depicts micrometer-scale raised platforms 540 separated by fluidic channels 520 that are in fluidic communication therebetween. The scale bar in FIG. 2C is 500 microns. As indicated above, a variety of nanometer-scale and micrometer-scale features may be imparted to the silk film from a mold or negative mold. The only limitation on the particular features that may be imparted is that the features must be able to be presented on a mold, and optionally on a negative mold, and transferred to the silk film or layer generated therefrom. It is understood that features may be completed, and/or further features may be imparted, by coupling a second film or layer to the first silk film or layer. The second film or layer may be any material, including silk, such as silk fibroin.

FIGS. 3A-3C are SEM images of the cross-sections of devices fabricated in accordance with the method illustrated in FIG. 1 and exemplified in FIG. 2C. In particular, FIGS. 3A-3C show exemplary microchannels 520 that are enclosed by two silk films bonded together. The width of the microchannel 520 in FIG. 3A is approximately 90 microns. The scale bar is 10 microns. The width of the microchannel 520 in FIG. 3B is approximately 240 microns. The scale bar is 200 microns.

Accordingly, features of silk-based microdevices (e.g., microchannels) may be fabricated to have various diameters, for example, less than about one millimeter; less than about 500 micrometers; less than about 250 micrometers; less than 100 micrometers; less than about 50 micrometers; less than about 10 micrometers; less than about 5 micrometers; less than about 1 micrometer; and/or less than about 500 nanometers. These dimensions may be obtained from the molding and bonding steps in fabrication, as described above.

FIG. 3C is a close-up SEM micrograph of the microchannel 520 outlined by box 550 in FIG. 3B, and illustrates a physically bonded interface (arrowheads 560) between two silk layers of the fabricated device. The front edge of the channel 520 is shown by broken line 570. The arrowheads 560 highlight the morphology of the silk fibroin at the interface. The scale bar in FIG. 3C is 5 microns. These micrographs demonstrate retention of microchannel geometries in thin films and a sealed interface between the two layers.

FIGS. 3D and 3E are fluorescent micrographs of patent microfluidic devices perfused with rhodamine solution (the scale bars are 500 microns and 50 microns in FIGS. 3D and 3E, respectively). Retention of the perfusate within the microchannels 520 indicates robust bonding at the interface. Accordingly, the lamination strategies described herein of bonding and/or laminating micromolded silk films using aqueous silk solution (see, e.g., FIG. 1B) represent an advantageous route for the microfabrication of patent microfluidic devices (FIGS. 2A-2C and 3A-3E).

3.3. Feature Geometry

The pattern of features in a silk-based microdevice may also be controlled in the molding and bonding steps of fabrication, as described above. The desired geometric patterns of features will vary depending on the use of the microdevice. As shown in FIGS. 2A-2C, features such as raised posts 510, microwalls 530, and/or raised platforms 540 may be fabricated in various patterns with high fidelity. Such features may also define a plurality of microchannels 520 fabricated in a repeated geometric pattern. The fabrication may yield a network of microchannels 520, some or all of which are in fluidic communication, as shown, for example, in FIGS. 2A and 2C. Alternatively, the fabrication may yield individual microchannels 520 with no fluidic communication therebetween, as shown in FIG. 2B. It is understood that the individual silk films shown in FIGS. 2A-2C may be coupled to a second and subsequent films) and/or layers comprised of silk or some other material.

Coupling the second layer (e.g., by the bonding methods described herein) to the first layer may produce enclosed microchannels. Enclosed microchannels as described herein generally refer to microchannels enclosed about the axial surface. Accordingly, in certain embodiments, a feature, such as a microchannel, is molded into the first silk film or layer, and a second film or layer is used to complete the feature, for example, to enclose the microchannel. However, in other embodiments, both the first silk film or layer and the second film or layer have features molded therein, such that when the films and/or layers are coupled, the features are complementary.

In one embodiment, the microchannel configuration depicted in FIG. 2C produces a constant maximum wall shear stress within all microchannels 520 in the device, given a steady volumetric flow rate. This device geometry may also be used in a microdevice comprising living cells, to assist in initial cell seeding by allowing cells to be evenly distributed throughout the device during attachment. Furthermore, the constant maximum wall shear stress design may facilitate rapid perfusion, while minimizing the potential detachment of seeded cells from shear forces.

3.4. Supporting Cell Growth

In certain embodiments, the methods and devices of the present invention support cell growth. A number of different cell types or combinations thereof may be supported in the silk films and/or layers, or on the surfaces of microfeatures, such as microchannels. Depending upon the intended function of the silk-based microdevice being produced, the cell types may include, but are not limited to, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

For example, smooth muscle cells and endothelial cells may be employed for generating muscular, tubular constructs within a microchannel, e.g., constructs intended as vascular, esophageal, intestinal, rectal, or ureteral constructs. Chondrocytes may be employed in cartilaginous constructs within a microchannel; cardiac muscle cells may be employed in heart constructs within a microchannel; hepatocytes and bile duct cells may be employed in liver constructs within a microdevice; and epithelial, endothelial, fibroblast, and nerve cells may be employed in constructs within a microdevice intended to function as replacements or enhancements for any of the wide variety of tissue types that contain these cells. In general, any cells may be employed that are found in the natural tissue. In addition, progenitor cells, such as myoblasts or stem cells, may be employed to produce their corresponding differentiated cell types within the microchannels.

Cells may be obtained from donors (allogenic) or from recipients (autologous). Cells may also be of established cell culture lines, or even cells that have undergone genetic engineering. Pieces of tissue may also be used, which may provide a number of different cell types in the same structure. Cells may be seeded within the silk film or layer either pre- or post formation, depending on the method of formation. Uniform seeding is preferable. In theory, the number of cells seeded does not limit the final tissue produced, however optimal seeding may increase the rate of generation. The number of seeded cells may be optimized using dynamic seeding.

Appropriate growth conditions for mammalian cells are well known in the art. Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth medium includes Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and the tissue desired.

In general, the length of the cell growth period will depend on the particular cells and purpose for the microdevice. The growth period may be continued until the microdevice has attained desired properties, e.g., until the microdevice has reached a particular thickness, size, strength, composition of proteinaceous components, and/or a particular cell density. Methods for assessing these parameters are known to those skilled in the art.

FIGS. 5A-5D are micrographs of various illustrative embodiments of cell-seeded silk microfluidic devices in accordance with the invention. As illustrated in FIG. 5A, silk microfluidic devices prior to cell seeding may be optically clear to permit observation via light microscopy (the scale bar is 100 microns in FIG. 5A). Cells (e.g., eukaryotic cells such as hepatocytes) may then be statically seeded (e.g., for four hours) at which time perfusion may commence. FIG. 5B shows a device seeded with human hepatocellular liver carcinoma cell (HepG2) that is partially confluent with cells exhibiting native morphology after 24 hours (the scale bar is 100 microns in FIG. 5B). FIGS. 5C and 5D are SEM micrographs of sectioned devices illustrating that viable cells remain attached and retain function within devices for up to 5 days of perfusion (the scale bars are 50 microns in FIGS. 5C and 5D).

In various embodiments, the methods and devices of the present invention support the growth of cells in their native morphology. For example, as shown in FIGS. 6A-6D, HepG2 is cultured on biomaterials including a silk film. HepG2 cells cultured on silk fibroin substrates appeared healthy and spread. HepG2 cells cultured on PLGA exhibited spheroid morphologies as observed through both phase contrast and SEM imaging. These morphologies are similar to that of hepatocytes cultured on PLGA substrates as observed by others. Scale bars in the phase images of FIGS. 6A and 6B are 100 microns, while the scale bars in the SEM images of FIGS. 6C and 6D are 10 microns.

Figure 7A:
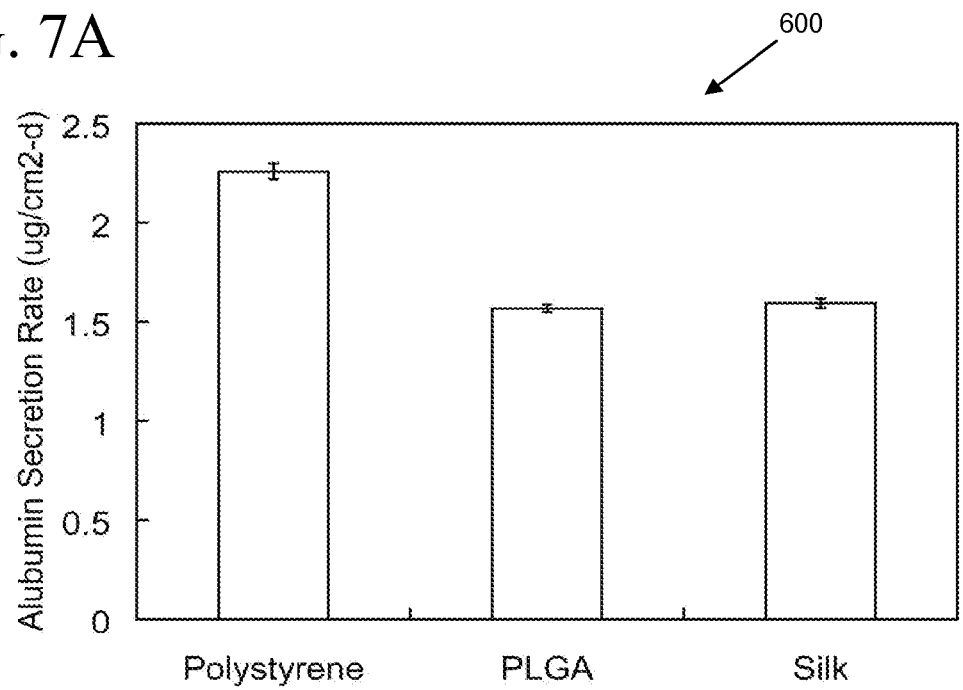
FIGS. 7A and 7B are graphs illustrating albumin secretion rates of seeded HepG2 cells in accordance with the invention.
Figure 7B:
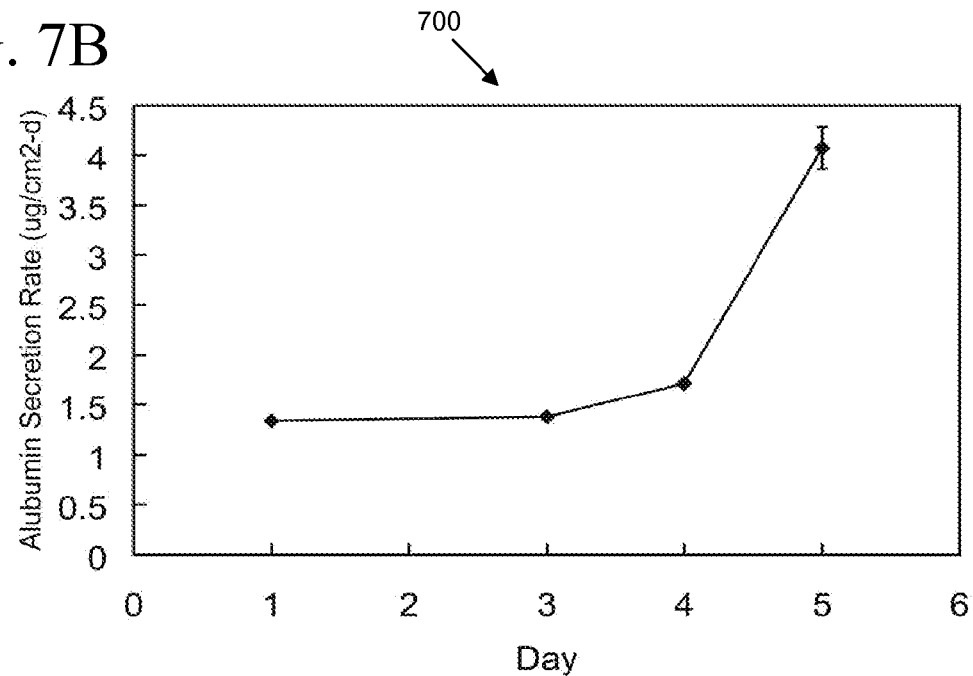

FIGS. 7A and 7B are graphs 600, 700 illustrating albumin secretion rates of seeded HepG2 cells in accordance with an embodiment of the invention. As illustrated in FIG. 7A, albumin secretion of HepG2 cultured on silk fibroin films was comparable to that of other biomaterial standards, including tissue culture polystyrene and PLGA. Furthermore, as illustrated in FIG. 7B, the albumin secretion rate of HepG2 cells cultured in silk fibroin microfluidic devices was similar to those cultured on silk fibroin films in static culture. The increase in albumin secretion across day 3 through day 5 likely is attributed to an increase in the growth rate of cells within the devices.

Oxygen diffusion limitations are typically of concern in the design and implementation of tissue engineered systems. Suitable perfusion rates have been characterized for the perfusion culture of HepG2 cells cultured in PGS microfluidic devices with similar length scales. Since silk films are found to have increased oxygen permeability over PGS membranes, the issue of sufficient oxygen supply and carbon dioxide removal is improved. These results shows that the morphology of HepG2 cells seeded and perfused in silk microdevices (FIGS. 5A-5D) is similar to that of HepG2 cells cultured on other biomaterials, including PGS. The liver-specific function of HepG2 cells cultured on silk fibroin was also determined to be similar across static and dynamic cultures. HepG2 cells cultured on silk fibroin films exhibited similar albumin secretion rates as those cultured on other typical biomaterials. Additionally, HepG2 cells cultured statically on films had similar albumin secretion levels to those cultured in dynamically perfused silk microfluidic devices (FIGS. 7A-7B).

4. Applications

In various embodiments, the devices (e.g,. microfluidic devices) described herein allow for the flow of liquids through the microchannels for diagnostic, therapeutic, or research purposes, and the ability to seed the microchannels with cells in order to create, for example, cell-based devices, assays, discovery tools, tissue constructs, and organ assist devices. Three-dimensional structures containing one or a plurality of layers of silk microchannel networks may also be fabricated, and the mechanical, chemical, and degradation-related properties of the microfluidic devices described herein may be tuned for various applications.

While reference is made herein to silk films and layers comprising features such as microchannels, these may be shaped into various articles, for example, for tissue engineering and/or tissue guided regeneration applications, such as reconstructive surgery. The microchannel surface may allow generous cellular ingrowth. However, the films and/or layers themselves may be fabricated to support cell growth. The films and/or layers may also be molded to form external scaffolding for the support of in vitro culturing of cells for the creation of external support organs.

In various embodiments, a silk-based film and/or layer of the present invention functions to mimic the extracellular matrices (ECM) of the body. For example, the silk-based film and/or layer may serve as a physical support and/or an adhesive substrate for isolated cells during in vitro culture and subsequent implantation. As the transplanted cell populations grow and the cells function normally, they begin to secrete their own ECM support and the silk-based microdevice may biodegrade. The biodegradation of the silk film and/or layer may be controlled by various manufacturing techniques known in the art.

All biomaterials used in connection with the devices described herein may be sterilized using conventional sterilization processes, such as radiation based sterilization (i.e., gamma-ray), chemical based sterilization (ethylene oxide), autoclaving, or other appropriate procedures. Preferably, the sterilization process will be with ethylene oxide at a temperature between 52-55° C. for a time of 8 hours or less. After sterilization, the biomaterials may be packaged in an appropriate sterilized, moisture resistant package for shipment and use in hospitals and other health care facilities.

5. Additional Materials

The silk films and layers described herein may comprise various components in addition to silk, for example polymers or therapeutic agents.

5.1. Polymers Added to Silk Solution

Biocompatible polymers may be added to the silk solution to generate composite silk films and/or layers. Biocompatible polymers that may be useful in embodiments of the present invention include, for example, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, and polyanhydrides. Two or more biocompatible polymers may be used.

In one embodiment, the film comprises from about 50 to about 99.99 parts by volume (vol %) aqueous silk protein solution and from about 0.01 to about 50 vol % biocompatible polymer, e.g., polyethylene oxide (PEO).

5.2. Therapeutic Agents

The devices described herein may also contain therapeutic agents, e.g., for administration thereof to a patient. To form these materials, the silk solution may be mixed with a therapeutic agent prior to forming the film and/or layer, or loaded into the silk firm and/or layer after it is formed. The variety of different therapeutic agents that may be used in conjunction with the devices described herein is vast and includes small molecules, proteins, peptides, and nucleic acids. In general, therapeutic agents which may be administered include, without limitation, antiinfectives, such as antibiotics and antiviral agents; chemotherapeutic agents (i.e., anticancer agents); anti-rejection agents; analgesics and analgesic combinations; anti-inflammatory agents; hormones such as steroids; growth factors (bone morphogenic proteins (i.e., BMP's), bone morphogenic-like proteins (i.e., GFD-5, GFD-7 and GFD-8), epidermal growth factor (EGF), fibroblast growth factor (i.e., FGF 1-9), platelet derived growth factor (PDGF), insulin like growth factor (IGF-I and IGF-II), transforming growth factors (i.e., TGF-.beta.-III), and vascular endothelial growth factor (VEGF)); anti-angiogenic proteins such as endostatin, and other naturally derived or genetically engineered proteins, polysaccharides, glycoproteins, or lipoproteins. Additionally, the devices described herein may be used to deliver any type of molecular compound, such as, pharmacological materials, vitamins, sedatives, steroids, hypnotics, antibiotics, chemotherapeutic agents, prostaglandins, and radiopharmaceuticals, proteins, peptides, nucleotides, carbohydrates, simple sugars, cells, genes, anti-thrombotics, anti-metabolics, growth factor inhibitor, growth promoters, anticoagulants, antimitotics, fibrinolytics, anti-inflammatory steroids, and monoclonal antibodies.

Silk films and/or layers comprising bioactive materials may be formulated by mixing one or more therapeutic agents with the silk solution used to make the film and/or layer. Alternatively, a therapeutic agent may be coated on the surfaces of the silk film and/or layer, for example the surfaces of microfeatures such as microchannels. The therapeutic agent may be applied with a pharmaceutically acceptable carrier. Any pharmaceutical carrier may be used that does not dissolve the silk material. The therapeutic agents may be present as a liquid, a finely divided solid, or any other appropriate physical form.

A therapeutic agent may be associated with the silk film and/or layer through any suitable means. For example, a therapeutic agent may be physically entrapped in or within the silk film and/or layer. Alternatively, a therapeutic agent may be chemically associated with the silk film and/or layer, for example, by hydrophobic, ionic, or covalent interaction and/or binding. Accordingly, delivery of the therapeutic agent may be a function of desorption of the therapeutic agent from the silk film and/or layer into a biological fluid. The rate of desorption may be altered by competitive adsorption of a biological chemical moiety to the silk film and/or layer, or by competitive interaction and/or binding between the therapeutic agent and a biological chemical moiety in the fluid phase (e.g. biological fluid). Delivery of the therapeutic agent may be a function of absorption of biological fluids into the silk film and/or layer, thereby expanding the silk film and/or layer and allowing release of the therapeutic agent entrapped in or within the film and/or layer. Moreover, delivery of the therapeutic agent may be a function of biodegradation of the silk film and/or layer to release the therapeutic agent, alone or in association with some portion of the degraded silk film and/or layer.

5.3. Agents Added to Enhance Cell Growth

The microchannel surfaces of the silk films and layers described herein may also be modified. For example, they may be coated with additives, such as bioactive substances that function as receptors or chemoattractors for a desired population of cells. The coating may be applied through adsorption, absorption or chemical bonding. In the latter case, the additives are immobilized on the microchannel surfaces.

Additives suitable for use with the devices described herein include biologically or pharmaceutically active compounds. Examples of biologically active compounds include, but are not limited to, cell attachment mediators, such as collagen, elastin, fibronectin, vitronectin, laminin, proteoglycans, or peptides containing known integrin binding domains, e.g., "RGD" integrin binding sequence, or variations thereof, that are known to affect cellular attachment; biologically active ligands; and substances that enhance or exclude particular varieties of cellular or tissue ingrowth. Agents that promote proliferation will be dependent on the cell type employed. For example, when fibroblast cells are employed, a growth factor for use herein may be fibroblast growth factor (FGF), most preferably basic fibroblast growth factor (bFGF) (Human Recombinant bFGF, UPSTATE Biotechnology, Inc.). Other examples of additive agents that enhance proliferation or differentiation include, but are not limited to, osteoinductive substances, such as bone morphogenic proteins (BMP); cytokines; growth factors such as epidermal growth factor (EGF), platelet-derived growth factor (PDGF), insulin-like growth factor (IGF-I and II) TGF-.beta., and the like. As used herein, the term additive also encompasses antibodies, DNA, RNA, modified RNA/protein composites, glycogens or other sugars, and alcohols.

One skilled in the art will understand that the methods and devices described above are general in nature and could be used for the advancement of the field of implantable and resorbable microfabricated systems, further expanding the impact of related technologies in biomedical applications. For example, the processing methodologies described herein may be used for the development of medical devices for a variety of in vitro and in vivo applications. In particular, various microfabricated silk devices that could be used for diagnostic systems and implantable devices that provide specific biological or medical function may be realized from this invention. In addition, while a silk based microfluidic device and methods for manufacture thereof have been described herein, the invention is not so limited. For example, other commercial applications of silk based micro-electro-mechanical devices could include vanishing tags or markers for tracking products, goods, animals, and humans for security and safety related reasons.

EXAMPLE

The following example describes a representative method for fabricating a microfluidic device from silk. Following fabrication of the device, fluid was flowed through the microchannels to confirm patent integrity. Cells were then seeded within the microchannels of the device and their function and morphology was assessed.

A. Materials and Methods

A.1 Preparation of Micromolded Silk Fibroin Films

Microfluidic networks with a constant shear design were chosen for device fabrication. The finalized mask layouts were converted to DXF files using AutoCAD 2000 and printed onto ½₀-mil transparencies (International Phototool, Colorado Springs, Colo.). Standard photolithographic and soft-lithography techniques were used in a mold-transfer process. Briefly, 100 mm diameter silicon wafers were patterned with SU-82 000 photoresist (Microchem, Newton, Mass.) according to the manufacturer's recommendations to produce a "positive mold." PDMS (Sylgard Elastomer Kit, Essex Group, Edison, N.J.) was cast on patterned SU-8 masters using a 10:1 (w/w) ratio of polymer to curing agent and cured for at least 3 hours at 65° C. Masters were passivated with a fluorocarbon treatment, and PDMS "negative molds" were delaminated and used for subsequent replica molding of silk fibroin films.

Aqueous silk fibroin solutions derived from Bombyx mori cocoons were prepared using a slight modification to previously published procedures. Briefly, cocoons were boiled for 30 minutes in an aqueous solution of 0.2M $Na_2CO_3$ to extract sericin proteins. The purified silk fibroin was dissolved in aqueous 9.3M LiBr at 60° C. for 3 hours to produce a 20% (w/w) solution. The concentrated silk fibroin solution was dialyzed against water in a Slide-a-lyzer cassette with a 3,500 MWCO (Pierce Biotechnology, Rockford, Ill.) for 48 hours. Final aqueous silk fibroin solutions were estimated to be 8% (w/w).

Silk solutions were cast on both microfabricated PDMS negative molds and flat PDMS substrates through water evaporation at room temperature and ambient humidity for 72 hours. Silk fibroin films were delaminated and treated with a methanol-water solution (50% v/v) for 4 hours to produce water-stable films, which then were washed in $ddH_2O$ for 24 hours. Samples for attenuated total reflectance FT-IR (ATR FT-IR) were prepared by first drying the film and mounting it on a crystal for film analysis. Spectra were recorded using a Nicolet Magna 550 Series II IR Spectrometer equipped with OMNIC Software using 32 scans across the wavenumbers 4000-400 $cm^{-1}$ at a resolution of 2 $cm^{-1}$. Surface roughness measurements were performed with a Wyko optical profiler (obtained from Veeco, Fremont, Calif.).

A.2 Mechanical Testing

PGS films for use in mechanical testing were prepared according to a known procedure. Briefly, a high molecular pre-polymer was thermally crosslinked onto sucrose-coated silicon wafers at 150° C. for 15 hours at a pressure of less than 50 mTorr. Sol-free films were cut into dog bone geometries with dimensions of 1 mm×6.5 mm×25 mm (T×W×L). Silk fibroin films dedicated for mechanical testing were cut into dog-bone geometries with target dimensions of 0.15 mm×6.5 mm×25 mm (T×W×L). Tensile testing was performed using an Instron 5542 with a 50N load cell equipped with Merlin software. Samples were extended at a constant rate of 50 mm/min and were elongated until failure. Young's modulus, toughness modulus, ultimate tensile strength and elongation at break were calculated from tensile stress versus engineering strain curves.

A.3 Silk Fibroin Device Fabrication

The strategy employed for microfluidic device fabrication was similar to that implemented in PDMS microfluidics. Briefly, silk fibroin sheets were trimmed and punched to achieve appropriate macroscopic fluidic connections between layers (FIGS. 1A-1B). Devices were fabricated by laminating micromolded and flat silk fibroin layers. Microfluidic layers were stacked, aligned, and bonded together at 70° C. for 18 hours under mechanical pressure using additional 8% aqueous silk fibroin solution at the interface. Silicone tubing (½₆" ID, ⅛" OD, Cole-Parmer, Vernon Hills, Ill.) was inserted into the devices in a sterile environment. Luer-Lok connections were inserted into the tubing and the base of the connections was sealed with epoxy (McMaster-Carr, New Brunswick, N.J.).

In some cases, additional PDMS structures were added to the inlet and outlet to prevent dissociation of the tubing from the device. Samples used from SEM were sputter-coated with Gold/Palladium using a Cressington 108 Auto sputter coater (Cressington Scientific Instruments, Inc., Cranberry Twp, Pa.). Scanning electron micrographs were taken using a Hitachi S-3500N at 5 kV. Fluorescent micrographs to demonstrate patency were obtained by flowing 100 µg/mL rhodamine in PBS solutions (Sigma, St. Louis, Mo.) through single layer devices.

A.4 Cell Culture

All cell culture products were obtained from Invitrogen, Inc., Carlsbad, Calif. unless otherwise noted. Hepatocyte carcinoma cells (HepG2, ATCC, Manassas, Va.) were cultured with Eagle's Modified Essential Medium supplemented with 10% fetal bovine serum, 25 mM HEPES, 100 µg/mL streptomycin, 100 U/mL penicillin, at 37° C. and 5% $CO_2$. Cells were harvested using Trypsin 0.025%/EDTA 0.01% and quenched with an equal volume of medium to resuspend the cells. Silk fibroin devices were prepared for seeding by incubating with medium for 4 hours at 37° C. immediately prior to cell seeding. The devices were statically seeded for 4 hours to allow for cell attachment using cellular concentrations of approximately $5\times10^8$ cells/mL. After this period, the devices were set up in a linear perfusion circuit consisting of a syringe pump (New Era Pump System NE-1600, Farmingdale, N.Y.), media reservoir, microfluidic scaffold, and media waste container. Fresh medium was perfused through single layer devices in a non-pulsatile manner with a volumetric flow rate of 150 µL/hr. Albumin samples were taken every 24 hours by sampling the waste container and aspirating the remaining medium to ensure the accuracy of future sampling.

Cells were fixed by injecting the device with Accustain fixative (Sigma, St. Louis, Mo.) manually with a syringe under high hydrostatic pressure. The sheets were sectioned and serially immersed in solutions of 25%, 50%, 75%, and 90% (v/v) ethanol in PBS for 5 minutes each. The samples were then immersed in 100% ethanol followed by HMDS (Sigma, St. Louis, Mo.) each for 15 minutes. The samples were then allowed to air dry for 24 hours prior to further SEM preparation, as previously described. Optical imaging was performed using a Carl Zeiss inverted microscope with Axio-Cam software. Polymer substrates for HepG2 albumin production were produced as follows. Briefly, thermal crosslinking of PGS prepolymer on to glass slides and solvent casting of 5% (w/w) solution of PLGA (65-35 High IV, Lakeshore Biomaterials, Birmingham, Ala.) in hexafluoroisopropanol (Sigma, St. Louis, Mo.) was used to produce PGS and PLGA films respectively. HepG2 cells were seeded at a density of 25,000 $cells/cm^2$. Albumin quantification was performed using a human ELISA quantification kit (Bethyl Laboratories, Montgomery, Tex.) with absorption measurements made at 450 nm wavelength using a SpectraMax Plus 384 (Molecu-lare Devices, Sunnyvale, Calif.) equipped with SOFTmax Pro 4.0 software. Albumin secretion rates were normalized by surface area of cell culture and volumetric flow rate, in the case of perfusion culture.

B. Results

Silk films derived from regenerated aqueous silk solutions exhibit FT-IR absorbance peaks that are characteristic of amorphous silk I structure, such as the amide I peak at 1656.6 $cm^{-1}$ and the amide II peak at 1541.5 $cm^{-1}$ (see, FIG. 4A). As illustrated in FIG. 4A, however, treatment of the silk films with aqueous-methanol solution may shift the peaks from the silk I configuration to a crystalline silk II configuration, as shown by the amide I and amide II peaks being shifted to 1616.3 $cm^{-1}$ and 1515.6 $cm^{-1}$. These peak shifts suggest an increase in the percentage of crystalline structure within the bulk. Fully hydrated water-stable silk fibroin films processed in this manner have been shown to increase β-sheet forma-tion, which results in increased stiffness, as determined by tensile Young's modulus, and an increased toughness modu-lus (see FIG. 4B), as well as an increased ultimate tensile strength over thermally crosslinked PGS films (see FIG. 4C). The following table compares the mechanical properties of regenerated silk fibroin and PGS films.

TABLE 1

Mechanical Properties of Silk Film

|  |  | Young's Modulus (MPa) | UTS (MPa) | Elongation at Break (%) | Toughness Modulus (MJ/m$^3$) |
|---|---|---|---|---|---|
| PGS | (n = 8) | 1.72 (0.79) | 0.281 (0.13) | 19.8 (1.11) | 0.0294 (0.0146) |
| Silk Fibroin | (n = 5) | 107.63 (18.29) | 7.60 (0.51) | 20.9 (0.16) | 1.21 (0.0118) |

Devices were fabricated from regenerated silk fibroin films that measured approximately 200 microns in thickness, which was controlled by the volume to surface area ratio during casting. The lamination strategy utilized aqueous silk fibroin solution to bond replica-molded water-stable silk films (see FIG. 1B).

Figures 8A, 8B:
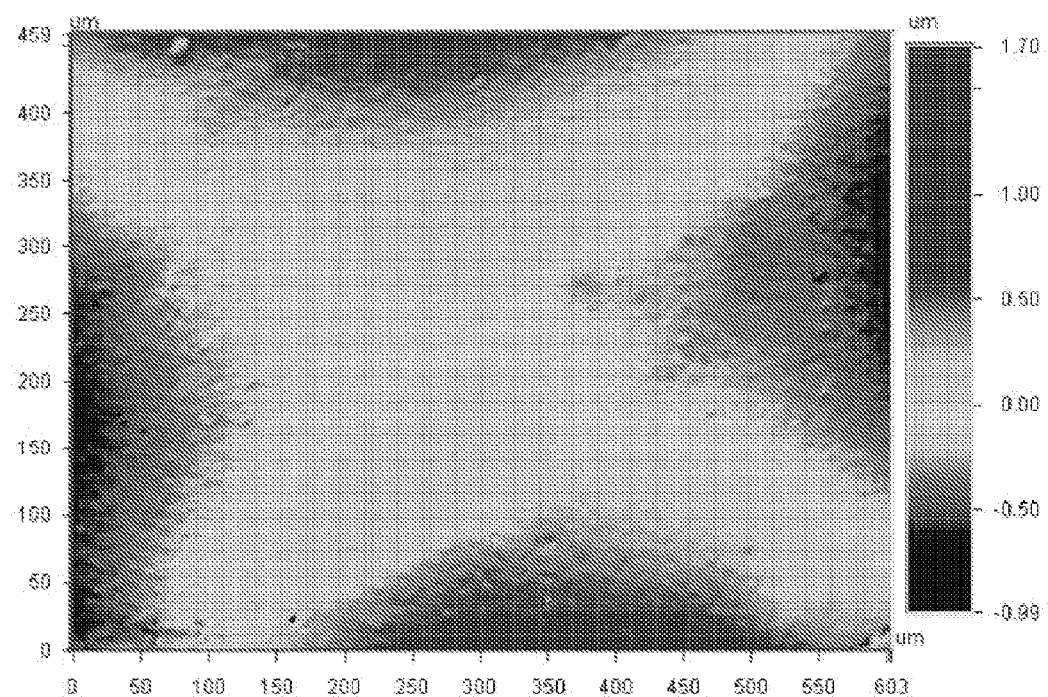
FIGS. 8A and 8B illustrate a surface roughness analysis of silk-fibroin films prepared in accordance with the invention.
Figure 9:
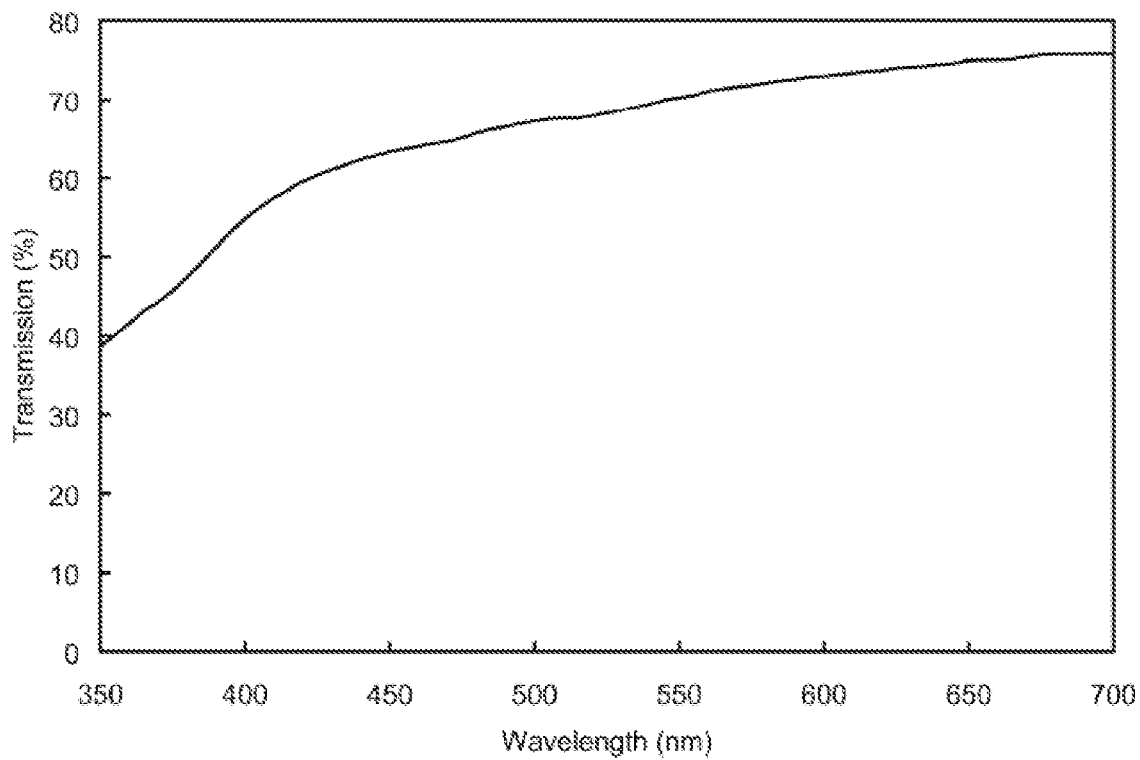
FIG. 9 illustrates an optical transmission spectrum of microfabricated silk fibroin films in accordance with the invention.

The average and root-mean-squared surface roughness of silk films after the lamination process was 216.6 nm and 267.4 nm, respectively, as shown in FIGS. 8A and 8B. FIG. 8A depicts an exemplary image of surface topography that was taken using a Wyko operated in VSI mode. FIG. 8B shows a statistical analysis including mean surface roughness (Ra), root-mean-squared (RMS) surface roughness (Rq), averaged peak-to-valley distance (Rz), and maximum peak-to-valley distance (Rt) that was taken in PSI mode across four different regions at 10× magnification. Replica-molded silk fibroin films cast on PDMS negative molds could be produced in rapid succession while maintaining a high degree of feature fidelity. Features as small as 400 nm could be produced using this method (see, e.g., FIG. 2A). Micromolded films (see FIG. 2C) were bonded to flat films to produce microfluidic devices (see FIGS. 3A-3C) that could support flow (see FIGS. 3D-3E). Occlusion of microchannels from excess aqueous silk fibroin solution during the bonding process at the inlet/outlet may contribute to reduced device yield.

The microfluidic layout used in this study was designed to produce a constant maximum wall shear stress within all microchannels in the device, given a steady volumetric flow rate. This device geometry assisted in initial cell seeding by allowing cells to be evenly distributed throughout the device during attachment. Furthermore, the constant maximum wall shear stress design facilitates rapid perfusion, while minimiz-ing the potential detachment of seeded cells from shear forces. The high cell seeding density resulted in the formation of HepG2 aggregates, which increased the opportunity for adhesion of cells to the microchannels. Suitable perfusion rates were characterized for the perfusion culture of HepG2 cells cultured in PGS microfluidic devices with similar length scales. The morphology of HepG2 cells seeded and perfused in silk fibroin microdevices (see FIGS. 5A-5D) was similar to that of HepG2 cells cultured on other biomaterials including PGS. Viability and liver-specific function of HepG2 cells cultured on silk fibroin were also determined to be similar across static and dynamic cultures. HepG2 cells cultured on silk fibroin films exhibited similar albumin secretion rates as those cultured on other typical biomaterials. Additionally, HepG2 cells cultured statically on films had similar albumin secretion levels to those cultured in dynamically perfused silk fibroin microfluidic devices (FIGS. 7A-7B). An increase in albumin secretion levels was observed from day 3 through day 5, which was likely due to increasing cell densities within the microchannels.

C. Discussion

As described above, the device fabrication methodology allows for the rapid and scaleable production of silk based microfluidic devices without the need for harsh processing conditions or cytotoxic compounds. The techniques employed in this methodology may be scalable by designing systems with increased surface area and lamination of mul-tiple layers. Moreover, the device yield for the patent devices described herein may be increased by designing flow layouts with redundant microchannel connectivity and by employing additional covalent bonding agents such as 1-ethyl-3-[3-dimehtylaminopropyl]carbodiimide hydrochloride ("EDC") and N-hydroxysuccinimide ("NHS"), an established chemi-cal route for bioconjugation of amines to carboxylates. Simi-lar techniques may also be used to covalently link peptides or other bioactive molecules both on the surface and throughout the bulk of the material of the device as has been shown for cell binding peptides and morphogens.

The aspects of device scalability and incorporation of bio-molecules may be important in the design and fabrication of tissue engineering scaffolds for highly vascularized tissue. These biodegradable microfluidic systems may also be inte-grated with existing biomaterial systems and technologies for tissue-specific applications and increased functionality. For example, drug delivery systems, cell patterning techniques, contact guidance cues, and co-culture systems for hepato-cytes may be integrated within the microchannels to promote the organization of seeded cells into complex tissues. The robust properties including a high toughness modulus and ultimate tensile strength could permit the use of silk based devices in dynamic mechanical environments associated with in vivo applications. In addition to the fabrication of microf-luidic systems, the methodologies for micromolding silk could be potentially useful in other BioMEMS devices including biodegradable drug delivery devices, scaffolds, or biosensors.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restric-tive.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The entire disclosure of each of the patent documents and publications disclosed hereinabove is expressly incorporated herein by reference for all purposes.

What is claimed is:

1. A microfluidic device, comprising first and second silk films coupled to define at least one microchannel there between, wherein at least a portion of the first silk film and at least a portion of the second silk film are bonded together by applying an aqueous silk fibroin solution to the surface of said first silk film, applying mechanical pressure to bring a surface of the second silk film into contact with the surface of the first silk film comprising said aqueous silk fibroin solution to form a composite, and heating said composite while applying mechanical pressure to form said microfluidic device.

2. The microfluidic device of claim 1, wherein at least one of the first and second silk films comprises silk fibroin.

3. The microfluidic device of claim 1, wherein the microchannel is molded into the first silk film.

4. The microfluidic device of claim 1, wherein a portion of a surface of the microchannel supports cell growth.

5. The microfluidic device of claim 4, wherein the portion of the surface of the microchannel supports the growth of cells in their native morphology.

6. The microfluidic device of claim 4, wherein eukaryotic cell growth is supported.

7. The microfluidic device of claim 4, wherein hepatocyte cell growth is supported.

8. The microfluidic device of claim 1, wherein the first and second silk films define a plurality of microchannels therebetween.

9. The microfluidic device of claim 8, wherein each microchannel has a diameter of less than 500 micrometers.

10. The microfluidic device of claim 8, wherein at least a portion of the plurality of microchannels are in fluidic communication.

11. The microfluidic device of claim 8, wherein at least a portion of the plurality of microchannels repeat a geometric pattern.

12. The microfluidic device of claim 11, wherein the repeated geometric pattern provides for a constant maximum shear stress at a steady volumetric flow rate within all the microchannels.

13. A method for transporting fluid, comprising:
providing the microfluidic device of claim 1 having first and second silk films coupled to define at least one microchannel therebetween, the microchannel comprising an inlet and an outlet; and
transporting fluid along the microchannel from the inlet to the outlet.

14. A method for growing cells, comprising:
providing the microfluidic device of claim 1 having first and second silk films coupled to define at least one microchannel therebetween;
flowing cell culture medium through the microchannel; and
seeding cells into the microchannel to allow the cells to adhere to a surface of the microchannel.

15. A method for treating tissue, comprising:
providing the microfluidic device of claim 1 having first and second silk films coupled to define at least one microchannel therebetween; and
applying the microfluidic device to tissue in vivo.

16. The method of claim 15, wherein applying the microfluidic device to the tissue results in regeneration of the tissue.

17. The method of claim 15, wherein the tissue is epithelial tissue.

18. The method of claim 15, wherein the tissue comprises at least one of epithelial cells, fibroblasts, or keratinocytes.

* * * * *